(12) United States Patent
Creighton, IV et al.

(10) Patent No.: US 6,630,879 B1
(45) Date of Patent: Oct. 7, 2003

(54) EFFICIENT MAGNET SYSTEM FOR MAGNETICALLY-ASSISTED SURGERY

(75) Inventors: Francis M. Creighton, IV, St. Louis, MO (US); Rogers C. Ritter, Charlottesville, VA (US); Andrew F. Hall, St. Charles, MO (US); Roger N. Hastings, Maple Grove, MN (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/497,467

(22) Filed: Feb. 3, 2000

Related U.S. Application Data
(60) Provisional application No. 60/118,959, filed on Feb. 4, 1999.

(51) Int. Cl.$^7$ ................................................. H01F 7/02
(52) U.S. Cl. .................................... 335/306; 335/304
(58) Field of Search ................................ 335/302–306; 324/318, 319, 320

(56) References Cited

U.S. PATENT DOCUMENTS

| | | | |
|---|---|---|---|
| 4,839,059 A | 6/1989 | Leupold | 335/210 |
| 4,869,247 A | 9/1989 | Howard, III et al. | 128/303.1 |
| 5,125,888 A | 6/1992 | Howard et al. | 600/12 |
| 5,216,400 A | 6/1993 | Leupold | 335/306 |
| 5,257,636 A | 11/1993 | White | |
| 5,312,321 A | 5/1994 | Holcomb | |
| 5,495,222 A * | 2/1996 | Abele et al. | 335/306 |
| 5,622,169 A | 4/1997 | Golden et al. | |
| 5,681,260 A | 10/1997 | Ueda et al. | |

OTHER PUBLICATIONS

13$^{th}$ Int. Workshop on RE Magents & Their Applications, "Construction and Evaluation of Permanent Magnet Variable Flux Resources", J.M.D. Coey and O. Gugat, pp. 41–54.

* cited by examiner

Primary Examiner—Ramon M. Barrera
(74) Attorney, Agent, or Firm—Harness, Dickey & Pierce, P.L.C.

(57) ABSTRACT

A system for magnetically assisted surgery includes a magnetic support structure, a patient support structure and a magnet having at least four poles attached to the magnetic support structure so that the magnet provides a near-field magnetic field in an operating region of a patient supported by the patient support structure. The magnet is moveable so that the direction of the magnetic field lines in the operating region is adjustable. The magnet may include a pair of essentially semicircular half-segments permanently magnetized and joined in an extremely stable disk configuration. The magnetic field and gradient field provided by the magnet is such that movement of the disk in one plane combined with rotation of the disk is sufficient to orient the magnetic field during surgical use, thereby reducing interference to medical imaging devices needed during surgery. An example of a medical delivery device that may be used for surgery in conjunction with this system is a flexible endoscope or catheter having a series of magnetically permeable rings.

13 Claims, 17 Drawing Sheets

EFFICIENT MAGNET SYSTEM FOR MAGNETICALLY-ASSISTED SURGERY

This Application claims the benefit of Provisional Application Ser. No. 60/118,959 Feb. 4, 1999.

FIELD OF THE INVENTION

This invention relates to systems for magnetically-assisted surgery and more particularly to systems for producing the magnetic fields required to guide surgically implanted magnetic medical devices.

BACKGROUND OF THE INVENTION

Several magnet systems to provide guidance for magnetic medical devices for navigation within a patient have been devised or are under development. An example of such a system is disclosed in commonly assigned application Ser. No. 09/189,633, "Articulated Magnetic Guidance System," which is hereby incorporated by reference in its entirety. A device disclosed therein includes a bed, a bed articulation system, a pair of x-ray sources, a coil or magnet articulation system, and an optional pair of additional magnets. The magnet articulation system comprises an articulation support, servo control mechanisms to provide movement of a coil or a permanent magnet along an arcuate arm both through a polar angle and in a radial direction. Optionally, the entire arm may also be pivoted through an azimuthal angle. The arm itself may comprise a track and gimbal assembly. Additional embodiments described in the referenced application include one in which the arm itself is moveable via an articulation support, another in which the magnet or coil is mounted on a pivotable ring support, and another in which the magnet or coil is mounted as an effector on a robotic arm. In the latter embodiment, it is desirable for the effector and all other parts of the robotic arm to be provided with exclusion zones to prevent accidental contact with a patient, with medical personnel, and, of course, with other items that might be damaged by such contact.

Other magnetic systems that provide guidance for magnetic medical devices within a patient are disclosed in commonly assigned application Ser. No. 09/211,723, filed Dec. 14, 1998, "Open Field System for Magnetic Surgery," which is also incorporated by reference in its entirety. A plurality of magnets are configured and arranged to provide a magnetic field effective within an operating region of a patient to navigate a magnetic medical device within the operating region while providing access to the patient for imaging and other purposes. A single magnet is arranged and configured to provide a magnetic field along at least one of a plurality of oblique axes extending through the operating region. One or more magnets are arranged and configured to provide a magnetic field along each of the other of the oblique axes. The magnetic fields generated by the magnets are effective to controllably navigate the magnetic medical device within substantially the entirety of the operating region. A preferred embodiment of the system described in this reference comprises three magnets in three mutually perpendicular planes, arranged so that their axes at least converge and more preferably intersect in the operating region. The magnets are arranged in an open configuration, so that the patient typically does not have to extend through a magnet coil to reach the operating region. In a preferred embodiment, the magnets comprise coils that are fixed with respect to one another in a generally downwardly facing hemispherical shell.

Still other magnetic systems providing guidance for magnetic medical devices navigated within a patient are disclosed in commonly assigned Provisional App. Ser. No. 60/095,710, filed Dec. 14, 1998, "Method and Apparatus for Magnetically Controlling Catheters for body Lumens and Cavities," which is also incorporated by reference in its entirety. The apparatus of the invention disclosed therein generally comprises a magnet system for applying a magnetic field to a magnet-tipped distal end of a medical device. The magnetic field provides a field that can navigate, orient, and hold the distal end of the medical device in the body. The apparatus also includes a computer for controlling the magnet system. Imaging devices connected to the computer provide images of the body part through which the catheter is being navigated. Displays are provided of these images. A controller connected to the computer has a joystick and a trigger to enable a user to input points on the displays for two-point and three-point navigation. The magnet system itself is preferably a set of electromagnetic coils that can be disposed around the body part to create a magnetic field of variable direction and intensity. Magnet systems suitable for such use are disclosed in U.S. Pat. Nos. 4,869,247, issued Sep. 26, 1989, "Video Tumor Fighting System," and 5,125,888, issued on Jun. 30, 1992, entitled "Magnetic Stereotactic System for Treatment Delivery," the disclosures of both of which are also incorporated by reference in their entirety.

In the commonly assigned application entitled "Device and Method for Specifying Magnetic Field for Surgical Applications," application Ser. No. 09/020,798, filed Feb. 9, 1998, and which is hereby incorporated by reference in its entirety, six normally conducting or superconducting coils are arranged in a rectangular box or helmet. With the Z-axis defined in the direction of the axial component of the head, the X- and Y-coil axes are rotated 45° from the sagittal plane of the head. Biplanar fluoroscopy cameras linked to a real-time host system are provided. Both cameras are calibrated to the six-coil host helmet design, in which three pairs of opposing coils on mutually perpendicular axes are provided. X-ray generators are also provided for the cameras.

In yet another commonly-assigned application entitled "Method and Apparatus Using Shaped Field of Repositionable Magnet to Guide Implant," application Ser. No. 09/020,934, filed Feb. 2, 1998, and which is herein incorporated by reference in its entirety, an apparatus comprising a moveable magnet assembly having a plurality of fiducial marks is disclosed. In an exemplary embodiment, the magnet assembly may be a gantry supporting either a strong permanent magnet or a superconducting electromagnet, although a strong permanent magnet may require additional articulation to compensate for its lack of current control and magnitude. The magnet assembly may be automatically controlled to provide the needed orientation, location and coil current required to align its magnetic field with the desired motion of a magnetic object to be guided. Localizers and camera-like sensors are provided to detect the fiducial marks on the magnet assembly, and additional fiducial markers may be placed on the patient's body. Medical imaging devices are used to display the location of the magnet relative to the volume of interest in the patient and the location of the implant. Various means are provided for moving the magnet.

Each of these devices and methods provides some success in being able to provide magnetic field orientations in all directions in sufficient strength for the intended applications. Nevertheless, even with specially designed systems, it is still difficult to completely avoid interference with the imaging system while achieving full functionality of the magnetic guidance system. In many of the above systems, this difficulty becomes apparent in the requirement to provide limitations in the movements of one or more large magnets or their supporting structures, or in limitations imposed on movements and positioning of an imaging system relative to the magnet system. In addition, the systems designed to date, including many of the above, have been quite large and expensive, or are restricted in purpose and application.

It would therefore be desirable to provide a relatively inexpensive system for magnetically assisted surgery that could produce a magnetic field in any orientation and at sufficient strength for use in medical applications. It would also be desirable if the system could provide field lines through a given procedure point in space (i.e., the location of the magnetic medical device) that could be easily and safely changed with a minimum of articulation of the magnet, so that the effect of the various exclusion zones in an operating region could be minimized.

SUMMARY OF THE INVENTION

The system for magnetically assisted surgery of a patient of this invention comprises a magnet support structure, a patient support structure, and a multipole magnet attached to the magnet support structure so that the magnet provides a near-field magnetic field in an operating region within a patient supported by the patient support structure. The magnet is moveable to alter the direction of magnetic field lines in the operating region of the patient. The magnet is preferably a quadrupole magnet, and may be a permanent magnet.

If the magnet is a permanent quadrupole magnet, it is preferably cylindrical, comprising a pair of essentially semi-circular segments joined so that the segments attract each other strongly in a highly stable arrangement. This arrangement would provide, in a region near a face of the magnet disk, a magnetic field essentially parallel to the face of the magnet disk, along the axis of the magnet. The magnet may be mounted so that it can be rotated on its axis and/or translated in one or more radial directions. A medical imaging system may also be provided and configured to provide a medical image of the operating region of a patient.

In accordance with a second aspect of the invention, a system for magnetically assisted surgery of a patient comprises a magnetic medical device configured to be implanted in a patient, a patient support structure, a magnet support base, and a magnet assembly adjustably supported on the support base and positionable thereon to provide a magnetic field of specified magnitude and direction and having a transverse gradient at the location of the magnetic medical device within the patient supported by the patient support structure. The magnet assembly may comprise a computer-controlled robotic arm having a magnetic effector, and the system may further comprise a medical imaging device configured to provide a relative location and orientation of the magnetic medical device in the patient and of the magnet assembly. The magnet assembly may itself comprise a permanent magnet, an electromagnet, or a superconducting electromagnet.

In some applications it is important to have a field in a direction approximately perpendicular to the "pulling" direction, i.e., the gradient direction. In some instances it would further be desirable to controllably change the relationship between the gradient direction and the field direction. One way of doing this efficiently is to use a multipole magnet, such as a quadrupole magnet. In such magnets, simple translation can change the field direction 90° while, since the gradient direction remains unchanged, changing the relationship between the field direction and the gradient direction. Another way of doing this efficiently is to use a simple magnet, and rotate it to use the side field. A simple magnet can be less expensive and stronger for a given weight than a multipole magnet, but there are occasions where the rotation required of a simple magnet might make the articulation more interfering with imaging and other medical apparatus in the surgical field.

The apparatus and method of this invention can thus provide for applying a directing magnetic field at any desired angle to a magnetic medical device within an operating region in a nearby patient, while simultaneously applying a pulling gradient in an essentially transverse direction to the orientation of the magnetic field.

The apparatus and method of this invention can also provide a method and apparatus for performing surgery on a patient by directing a magnetic medical device, such as a catheter or endoscope having a magnetic or magnetically permeable tip, in a direction perpendicular to the magnetic field. Thus, the magnetic medical device axis is easily oriented, even with modest or weak magnetic fields.

The apparatus and method of this invention can also provide an external magnet system for magnetically assisted surgery that will provide an orienting field and transverse gradient for stable and reliable movement of a magnet medical device.

The apparatus and method of the invention can also provide an external magnet system for magnetically assisted surgery using a magnetic medical device, in which the direction and strength of the magnetic force on the magnetic medical device may readily be controlled by a surgeon.

Finally, the apparatus and method of this invention can provide a magnet system for magnetically assisted surgery that minimizes the limiting effect of exclusion zones on the ability of the magnet system to provide magnetic fields of selected direction and strength within.

The manner in which these and other features of the invention are achieved will become apparent to one skilled in the art upon study of the accompanying figures and description.

BRIEF DESCRIPTION OF THE DRAWINGS

Although the figures are intended to be illustrative, it should not necessarily be assumed that the figures are drawn to scale. Corresponding reference numerals indicate corresponding parts throughout the several views of the drawings.

DETAILED DESCRIPTION OF THE PREFERRED EMBODIMENT

Figure 1:
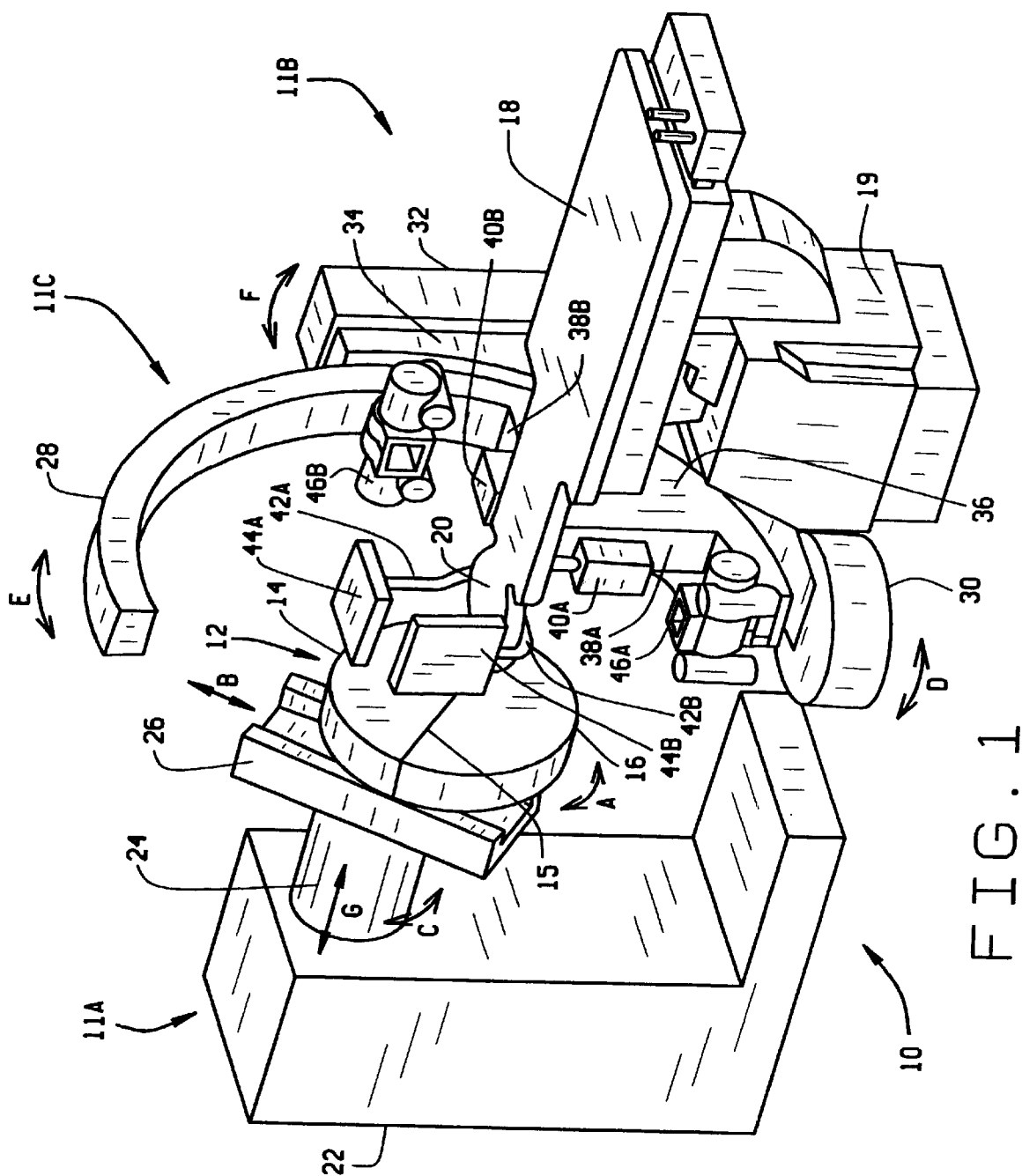
FIG. 1 is a perspective view of an embodiment of a system for magnetically assisted surgery in accordance with the invention.

FIG. 1 is a drawing of a system 10 for magnetically-assisted surgery. The system generally comprises two sections; a magnet assembly 11A and a patient support 11B. Magnet assembly 11A comprises a magnet 12 that is located or brought into proximity with an operating support region 20 of patient support 11B.

Magnet assembly 11A comprises a magnet 12, preferably having more than two poles, and which is preferably a quadrupole magnet in the form of a disk or cylinder having two semi-cylindrical segments 14 and 16 joined magnetically at a seam 15 coincident with a diameter of the cylinder. Each of the half segments 14 and 16 are magnetized in different directions so that the two segments attract each other with great force when assembled into a disk to thereby form a very stable mechanical system. While other forms of quadrupole magnets can provide similar results, the form of magnet 12 shown in FIG. 1 and which is described in more detail below provides remarkable simplicity and efficiency. Although a quadrupole magnet is believed preferable, magnets or assemblies of magnets having more than four poles could be substituted for magnet 12 within the scope of the invention.

Figure 2:
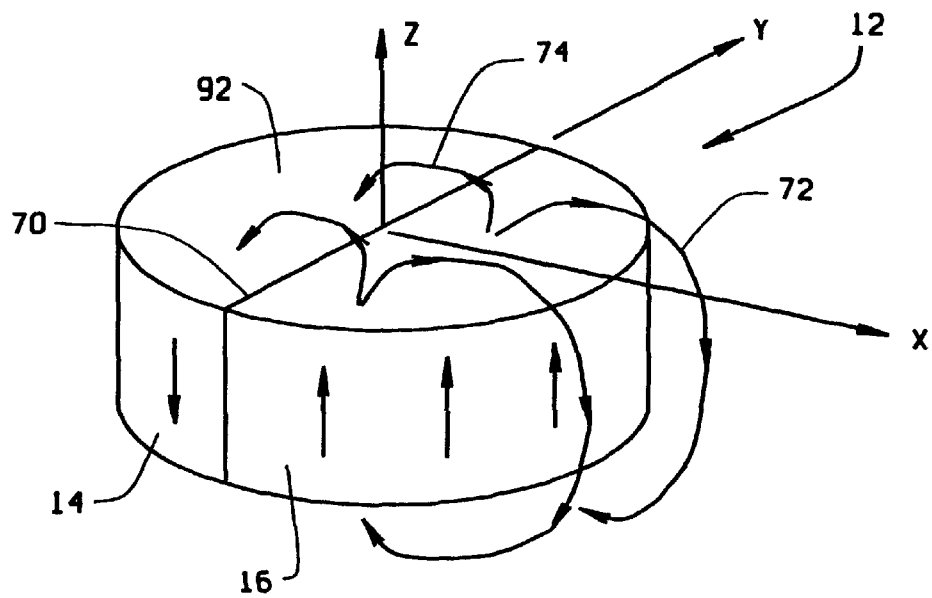
FIG. 2 is a perspective view of the magnet assembly of FIG. 1.

FIG. 2 shows how the half segments of the magnet cylinder 12 are magnetized to provide advantages in accordance with this invention. The axis of the cylinder 12 is taken as the Z axis, while the seam 70 that joins the half segments 14 and 16 arbitrarily defines a Y direction. The X direction is taken as being perpendicular to the Y direction and the Z axis. On one side of seam (15)70, half segment 14 of magnet disk 12 is magnetized in the −Z direction, while half segment 16 of magnet 12 is magnetized in the +Z direction. As indicated above, there is a considerable magnetic force holding the two half segments 14 and 16 together along seam (15)70, making magnet disk 12 a very stable structure.

FIG. 2 also shows a few of the magnetic field lines 72, 74 of magnet 12, the arrangement of which provide special features of the system. It is known that the distant field strength of a quadrupole falls off with distance by one power greater than that of the dipole. Therefore, one might expect that quadrupole magnets would be less useful than dipole magnets in surgical applications, where large magnetic fields are frequently required. However, for medical and surgical applications, the system described herein takes surprising advantage of the magnetic field lines in the near and transition fields of the quadrupole magnet 12.

Figure 3A:
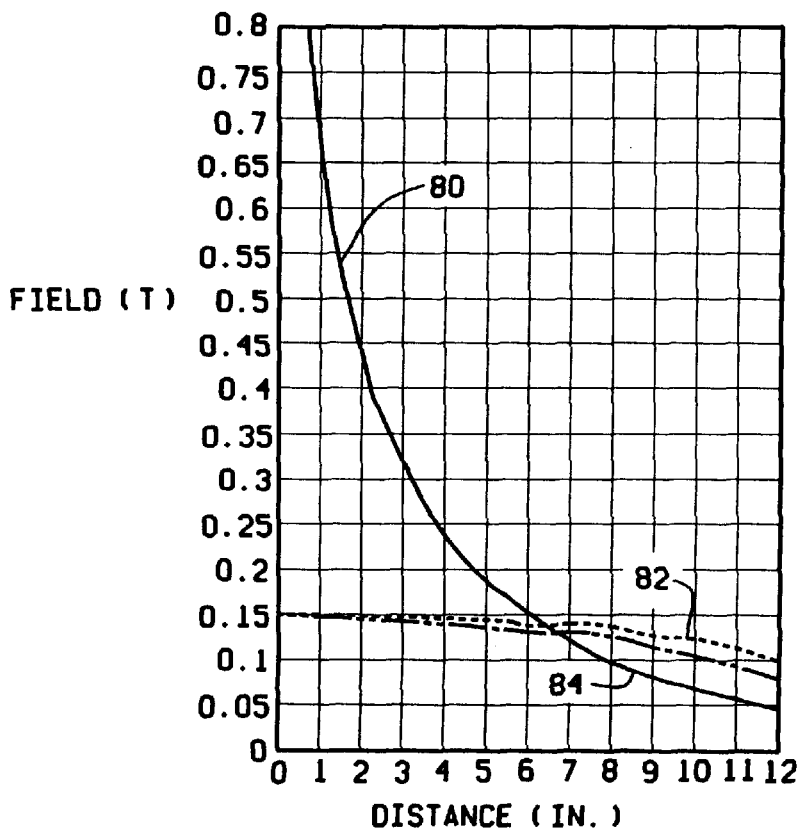
FIG. 3A is a graph showing relationships of magnetic field strength and distance along the axes of a cylindrical quadrupole magnet.
Figure 3B:
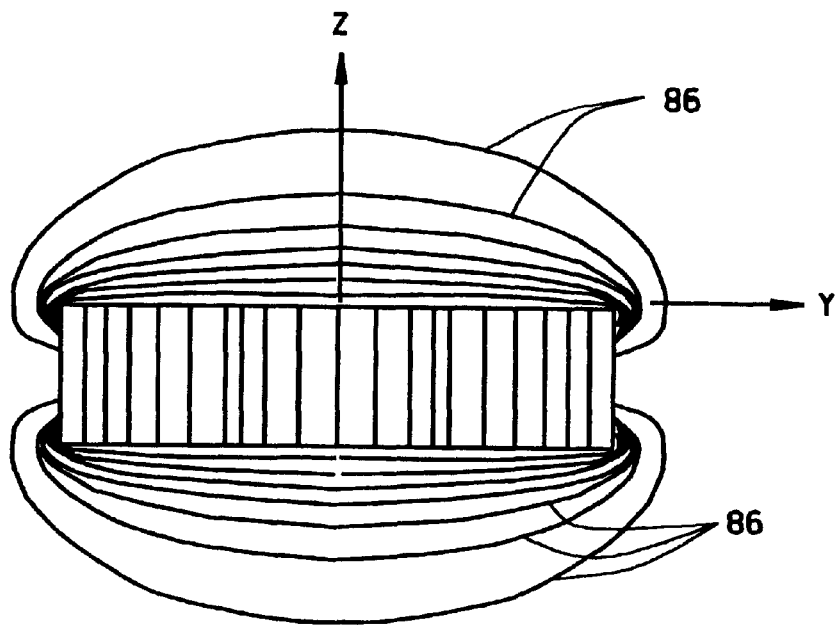
FIG. 3B is a graph showing contours of equal field strength when the magnet of FIG. 2 is viewed from the −X direction.

To provide an effective magnetic field for surgical applications, quadrupole magnet 12 may preferably comprise a NdFeB magnet of 44 MgOe maximum energy, having a radius of 12.39 inches and a thickness of 6.20 inches. In this case, quadrupole magnet 12 would weigh about 800 pounds and could be permanently magnetized to achieve a field strength along the Z axis of about 0.15 Tesla at 6 inches from its face 92. FIG. 3A is a graph of the magnetic field strength in Tesla calculated for this cylindrical quadrupole magnet 12 along the three axes of the magnet; line 80 shows the strength along the Z axis, and lines 82 and 84 show the strength along the X and Y axes, respectively. Contours 86 of equal field strength when viewing magnet 12 towards the −X direction are illustrated in FIG. 3B, while contours 88 of equal field strength when viewing magnet 12 towards the +Y direction are illustrated in FIG. 3C.

Figure 3C:
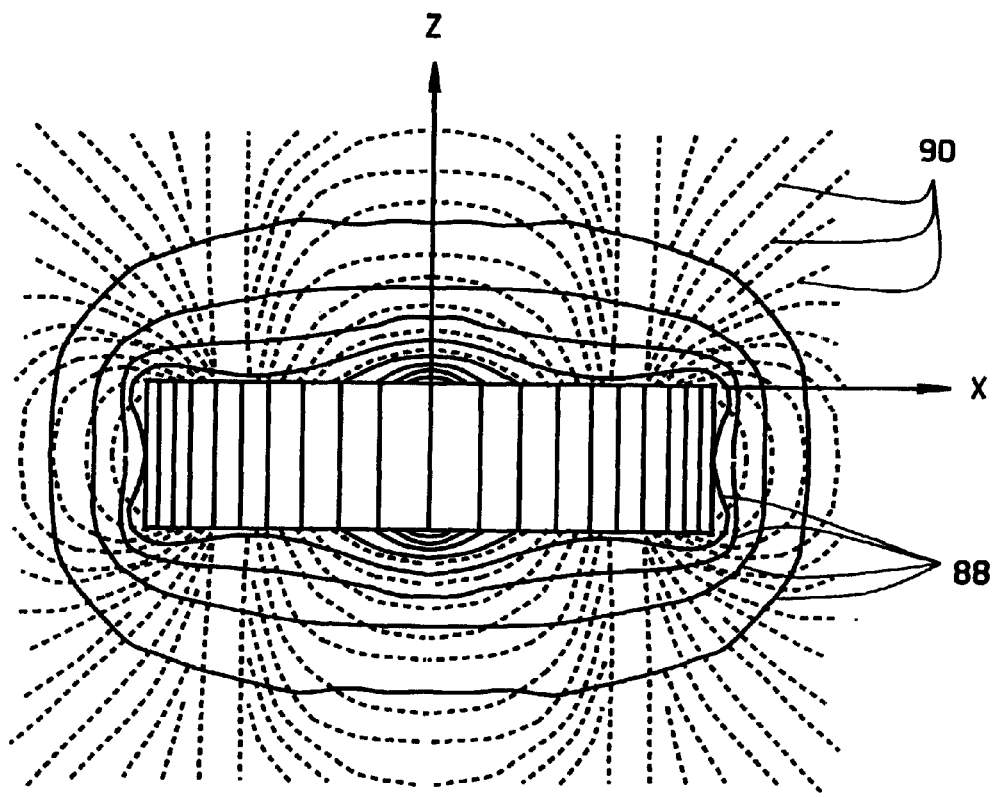
FIG. 3C is a graph showing contours of equal field strength when the magnet of FIG. 2 is viewed from the +Y direction.

The multitude of small arrows 90 in FIG. 3C represents magnetic field directions on a grid of points. The arrangement of field line directions crossing the Y–Z plane (the plane of seam 70) are parallel to face 92 of the magnet as seen in FIG. 2. Therefore, a rotation of magnet 12 about the Z axis will change the magnetic field direction at any point on the Z axis while maintaining the same strength. It is thus possible to rotate the magnetic field direction along the Z-axis by 360° or any portion thereof without an accompanying translation of quadrupole magnet 12. On the other hand, translation of the quadrupole magnet 12 along the X axis by slightly over half of its radius will turn the magnetic field so that it is directed along the −Z direction. The same translation along the −X axis will turn the field so that it is oriented in the +Z direction. It will thus be apparent that complete control of magnetic field direction in an operating region of a body for medical and surgical applications can be achieved by, at most, two translations and one rotation, or two rotations and one translation of quadrupole magnet 12. Such an operating region of a body could include a person's head, as for magnetically assisted brain surgery. Although not shown in the figures, it may be advantageous in some applications to mount magnet 12 so that its Z axis may also be tilted. In use, the patient's operating region will be in the near field of magnet 12.

Figure 4:
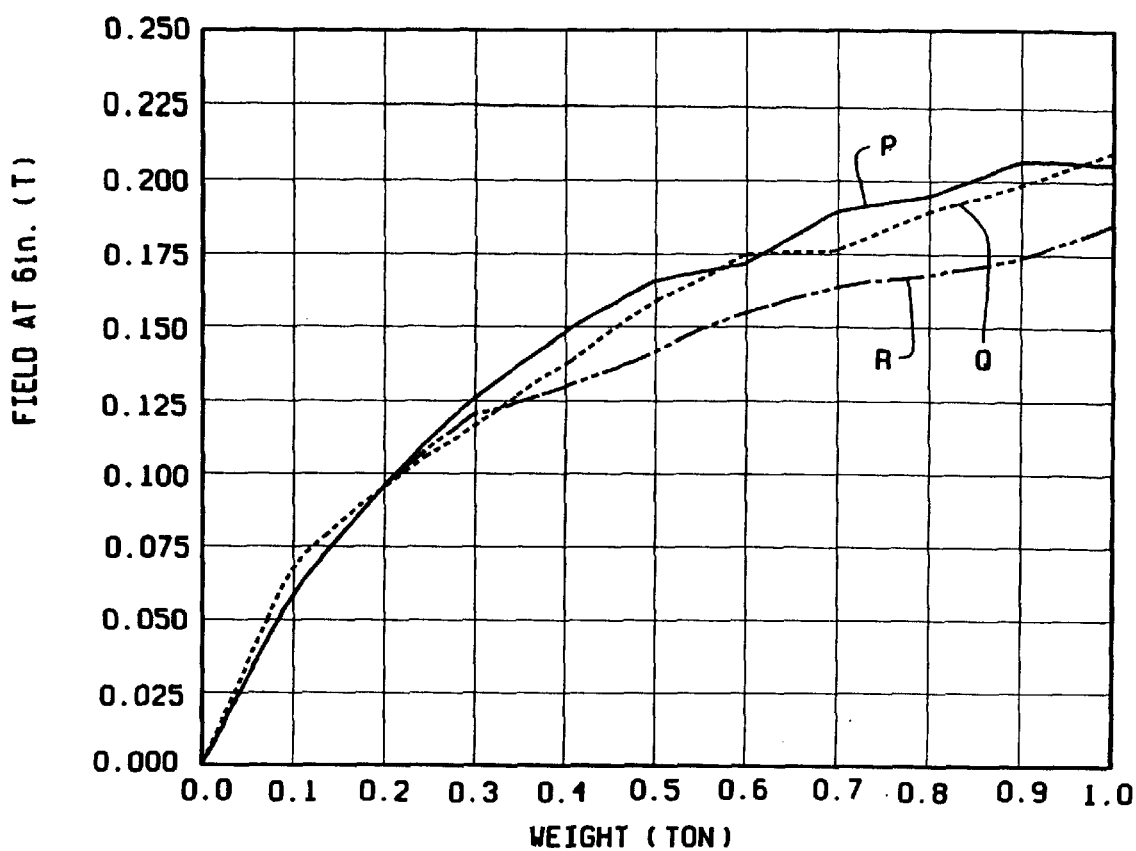
FIG. 4 is graph showing the relationship of the calculated weight of the magnet of FIG. 2 to its calculated magnetic field at a distance six inches from its face.

Because cost and navigation efficiency are partly determined by size and weight, FIG. 4 provides a plot showing the relationship of the calculated weight of magnet 12 to its calculated magnetic field at a distance 6 inches from its face. The plot has been calculated for three different aspect ratios (i.e., the ratio of radius to thickness). Line P is for an aspect ratio of 1.0; line Q is for an aspect ratio of 2.0; and line R is for an aspect ratio of 4.0.

Referring again to FIG. 1, magnet 12 is preferably rotatably mounted on a track 26. This mounting allows two independent movements of magnet 12, one being a rotation on the axis of the magnetic disk 12 shown by arrow A, and the other being translation along track 26 as indicated by arrow B. Preferably, track 26 itself is also rotatable about an axis as indicated by arrow C. This additional rotation may be provided by mounting track 26 on a shaft 24 that is rotatably mounted on the support base 22 of magnet assembly 11A. Shaft 24 may also be slidable along its axis to thereby provide another direction of motion that permits magnet 12 to be withdrawn from proximity to the operating region of the patient. This motion is indicated by arrow G in FIG. 1.

The embodiment of magnet assembly 11A in FIG. 1 thus provides a quadrupolar magnet 12 that is or that may be brought into close proximity with an operating region of a patient. Quadrupole magnet 12 may be subject to a plurality of rotational and translational movements to provide differing magnetic field orientations in the operating region. Translation in three dimensions (including withdrawal from the operating region) is provided in the embodiment of FIG. 1. In other embodiments, it may be possible to mechanically tilt the axis of the magnet with respect to the operating region. Although tilting may be desirable in some operating situations, it is not necessary to practice the invention.

Magnet assembly 11A may comprise a robotic support manipulator to provide the rotation and translation of magnet 12, and may optionally also provide tilting of the Z axis of magnet 12. Because of the weight of magnet 12 and for other reasons, as well, robotic control is preferable to full manual movement of magnet 12, although manual control is both possible and contemplated within the scope of the invention. The movements required of the robotic manipulator are those that are required to make possible the movements of magnet 12 as described herein. Robotic manipulators are well-known in the art, and the design of servo mechanisms to provide the needed movements of magnet 12 would present no special difficulties to one skilled in that art. Such servo mechanisms could be manually controlled by a surgeon viewing real-time medical images of the operating region of a patient, or could be automatically controlled by a computer interpreting such images. If manually controlled, a computer could provide assistance by displaying medical images of the operating region of the patient, showing the magnetic delivery vehicle (MDV) or magnetic seed in the patient with other useful information superimposed or adjacent to this image. This other information could include a desired path of the MDV or magnetic seed and the magnetic field lines or gradient of magnet 12.

FIG. 1 illustrates a patient support essentially identical to that described in copending application Ser. No. 09/211,723, filed Dec. 14, 1998, and incorporated by reference above. Patient support 11B comprises a bed 18 that is supported at a convenient operating level by a base support 19. Bed 18 includes a region 20 that is or can be brought into proximity with magnet 12. (Although it is contemplated that the magnet 12 will be moveable, movement of the operating region of a patient relative to magnet 12 may alternately, in some circumstances, be accomplished by moving the bed 18 supporting the patient.) Also provided is a rotating pivot or swiveling support 30 on which is attached an imaging assembly 11C comprising a base frame 32, arcuate support 34, and arcuate section 28. Part of imaging assembly 11C may comprise any suitable, commercially available C-arm assemblies, such as those made by General Electric Co. of Syracuse, N.Y., however, it is not required that the "arcuate" section be in the shape of an arc. Because commercially available C-arm assemblies usually are this shape, however, it is convenient to use this terminology. Support 30 need not be mounted or free-standing on a floor, as shown here. Some other mounting possibilities include attachment of support 30 to an extension of base support 19 of patient support 11B, or to an extension of support base 22 of magnet assembly 11A. Mountings that do not require movements of imaging assembly 11C that interfere with the attached imaging apparatus described below when magnet 12 is repositioned are preferable.

Arcuate section 28 supports one or more X-ray or fluoroscopic tubes 46A and 46B for use in providing a medical image of the operating region of the patient supported at region 20 of bed 18. Thus, each of the tubes 46A and 46B have their beams aimed at corresponding imaging plates 44A and 44B through this region. Preferably, imaging plates 44A and 44B are held in place by imaging plate supports 42A and 42B, respectively, which are separate supporting arms. The position of these plates may be adjusted somewhat by moving blocks 40A and 40B, respectively, which are configured to slide (such as on tracks, not shown in FIG. 1), over surfaces 38A and 38B of a pie-shaped portion 36 of arcuate support 28.

Figure 5:
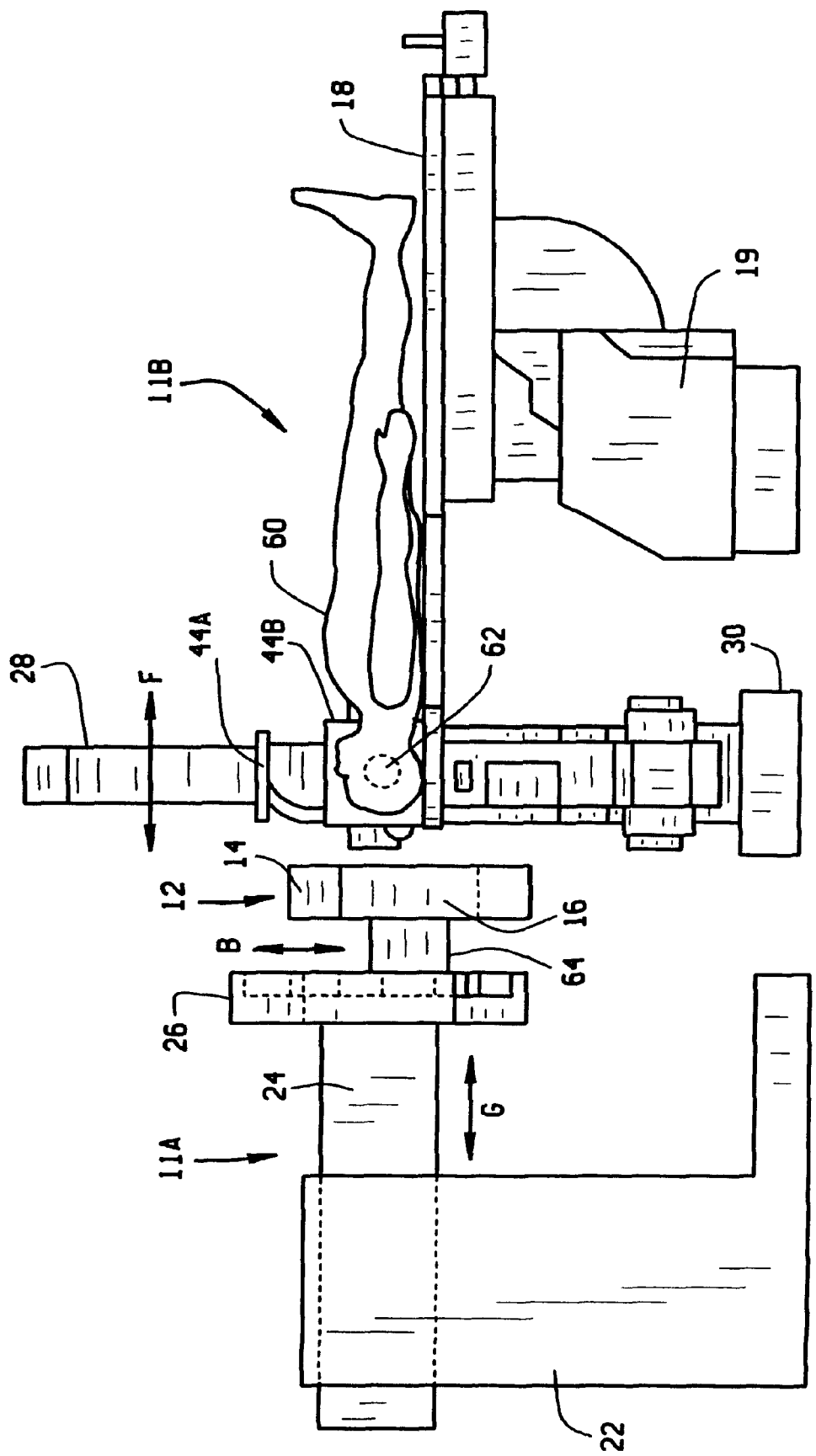
FIG. 5 is side view of the apparatus shown in FIG. 1, showing some of the movements of both the magnet assembly and the patient support relative to an operating region of a patient.

Some of the pivoting and movement mechanisms of the C-arm and imaging assembly 11C are not shown in FIG. 1, but are shown and described in application Ser. No. 09/211, 723. Briefly, arcuate section 28 is configured to provide various views of an operating region of a patient by pivoting at swivel support 30 (shown by arrow D), partial rotation around another pivot (as shown by arrow F, along an axis preferably perpendicular to the pivoting axis at 30), and by partial rotation of the entire arcuate section 28 around a central point, as indicated by arrow E. Each movement of arcuate section 28 also causes the imaging tubes 46A and 46B and their respective imaging plates to move correspondingly relative to the operating region of the patient, which is not operatively coupled to these C-arm movements. Thus, various views of the operating region are available. Some of the movements of both magnet assembly 11A and patient support 11B may also be seen in FIG. 5, which also shows where an operating region 62 of a patient 60 would be situated in relation to the parts of the inventive apparatus. It will be recognized that the views provided by the imaging devices can provide the relative locations of magnet assembly 11A, a medical delivery device in a patient 60, and an operating region of the patient 62.

It will be observed that movement of the arcuate section 28 and the objects attached to it result in physical exclusion volumes being created. These are regions of space that are or may be occupied by the moving components, and that must therefore be avoided by movements of the magnet 12 or magnet assembly 11A. If the physical exclusion volumes are not respected, physical interference between the components of the system occur. It may also be useful to consider magnetic as well as physical exclusion regions. Magnetic exclusion regions are regions from which, taking into account the movement of magnet 12, magnetic objects or objects that may be adversely affected by magnetic fields should be excluded. Thus, it may be desirable to avoid placing some types of imaging plates 44A and 44B within a region of high field strength of magnet 12. However, because of the relatively small size of quadrupole magnet 12 and the requirement of only limited rotational and translational movement, both its physical and magnetic exclusion zones are advantageously quite small. Additionally, because magnet 12 is a quadrupole magnet, the magnetic exclusion zone is smaller than might otherwise be the case, because the magnetic field generally drops off more quickly with distance for such magnets than with the dipole magnets and solenoids previously used. (Similar advantages may be obtained with magnets having more than four poles.)

Figure 6:
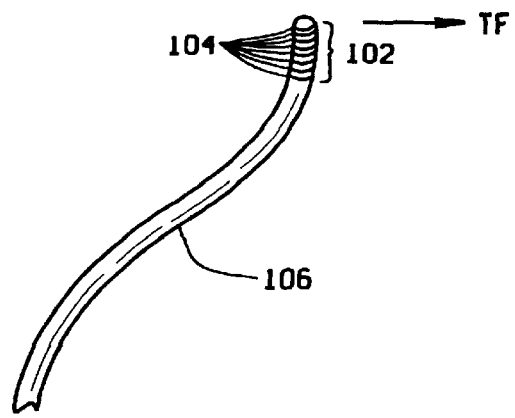
FIG. 6 is an illustration of a magnetic medical device that may be introduced into a patient and used in conjunction with the magnetic surgical systems of this invention.

The inventive system described herein is intended for use in magnetically assisted surgery. For example, it may be used to guide a tiny magnet on the end of a catheter or guide wire that is magnetically navigated into an aneurysm in the brain. A magnetic medical device 102, as illustrated in FIG. 6, may be introduced into an operating region 62 of a patient 60 in accordance with this invention. Magnetic medical device 102 may comprise a series of magnetically permeable rings 104. These rings may be mounted on a slightly flexible rod 106, such as a catheter or endoscope. The individual moments of the rings are induced to be along the direction of the magnetic field of magnet 12, and this orientation is not altered by the gradient of the field. Instead, the gradient and the direction of the field may be used in a complementary way so that the axis 108 of the magnetic medical device is easily oriented, even with the application of modest or weak magnetic fields from the external magnet 12. At the same time, the transverse gradient applies a transverse force TF on the moment of the system.

Magnet assembly 11A and patient support 11B as shown and described herein are physically separate assemblies, but it should be clear that this is not a requirement of the invention. It is also not necessary that patient support 11B be in the form shown here. Any form of supporting structure suitable for holding or supporting an operating region of a patient may be used, possibly including a floor in an emergency, with suitable modification of either or both magnet assembly 11A and imaging assembly 11C so that the magnet may be appropriately positioned and the operating region properly imaged. In the claims appended below, it should be understood that a magnet support structure and a patient support structure need not be physically separate assemblies, and that, unless explicitly stated otherwise, the magnet support structure and patient support structure may comprise different portions of a single structure.

In alternate embodiments, a magnet may be attached to a flexible or articulated arm that is attached to the ceiling, rather than to a support structure such as shown in FIG. 1 that is attached to or supported by the floor. A ceiling mounted assembly would avoid congestion at the floor area of the patient. Moreover, the flexible or articulated arm may be designed to allow easy manual or adjustment of the position and angle of the magnet assembly. Alternately, the ceiling supported assembly could be robotically controlled.

In another alternative embodiment, the transverse magnitude and gradient fields may be generated by an electromagnet rather than a permanent magnet. It is a general characteristic of coil systems having standard symmetries (i.e., that are symmetric about the coil axis and symmetric with respect to a center, equatorial plane of the coil) that in regions in and near the equatorial plane, both inside and outside the coil, a magnetic field exists that is parallel to the coil axis, while at the same time a transverse gradient of the field is perpendicular to the axis. For example, a single circular turn of wire in a plane has such a field and gradient relationship. However, for such a coil, the region inside or outside the coil at which this relationship occurs is too narrow to be useful. Attempts to use such a coil to magnetically assist a surgical procedure employing a magnetic medical device will be subject to error due to operator inaccuracy.

Appreciable regions around a long solenoid coil (with either normally conducting or superconducting turns) will have an essentially transverse relationship of field and gradient. However, the field and gradient will be relatively weak for a given number of ampere-turns of the coil. However, upon recognizing the advantages of providing the transverse field and gradient relationship in accordance with this invention, one skilled in the art would be able to optimize the design of a coil for use in conjunction with the invention. Such a coil would have a sufficiently large region in which the required relationship exists, at a suitable distance from the coil for use in a desired surgical application. Permanent magnets may also be designed with similar characteristics, although different mathematical tools may be required. The quadrupole magnet 12 described in detail above is one particularly simple and advantageous permanent magnet design in accordance with this invention.

Figure 7:
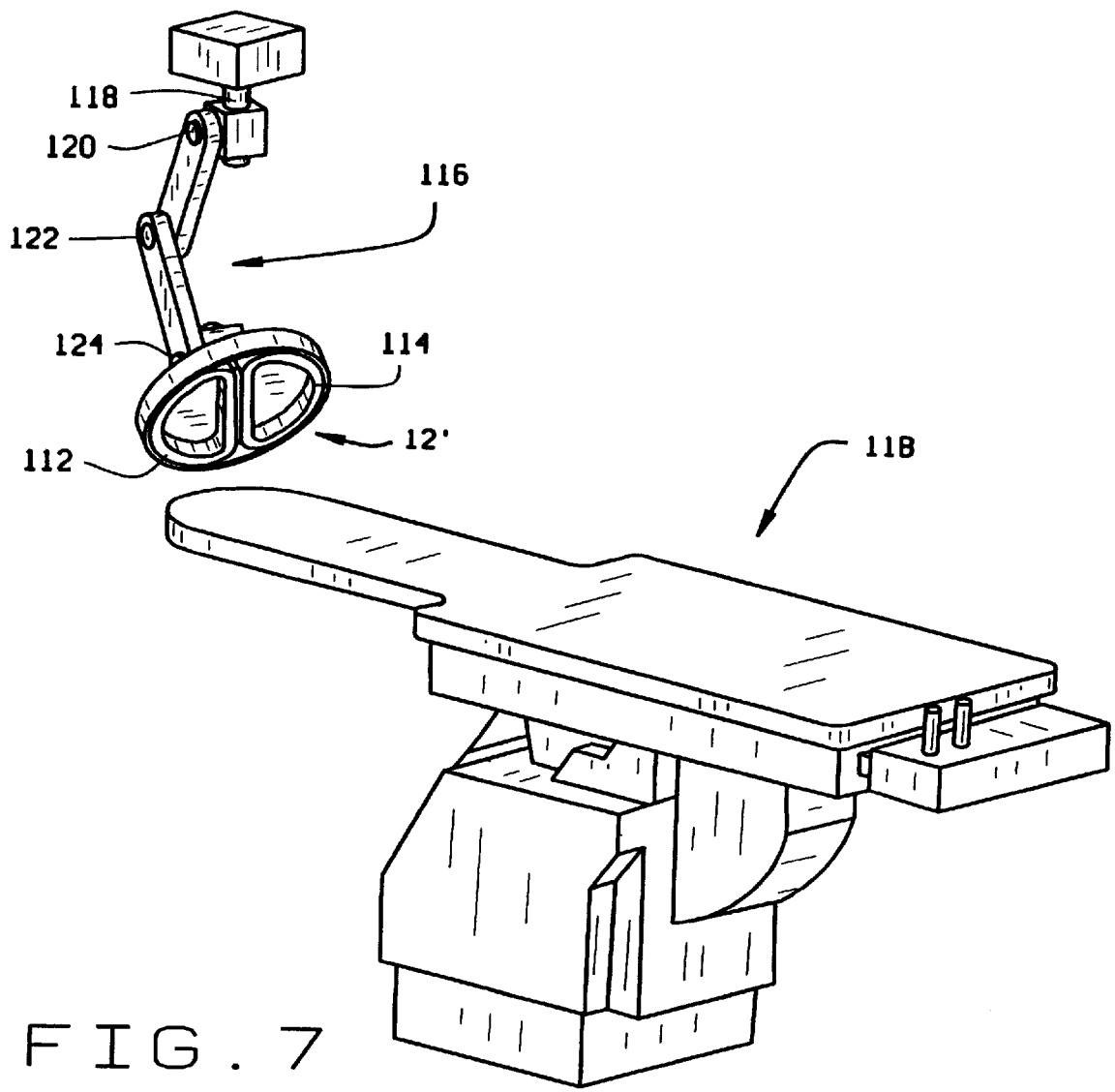
FIG. 7 is an isometric, schematic illustration of an embodiment of the system for magnetically assisted surgery employing a quadrupole electromagnet.

Notwithstanding the above remarks, it is possible to configure two or more (preferably superconducting) electromagnets to achieve many of the advantages of the permanent quadrupole magnet 12 discussed above, as well as some additional advantages. Such a configuration is represented isometrically (and somewhat schematically) in FIG. 7. Referring to FIG. 7, quadrupole magnet 12' comprises a pair of preferably D-shaped coils 112, 114 mounted at an end of an articulated arm 116. The straight sections of coils 112 and 114 are preferably closely adjacent to one another, as shown. Articulated arm 116 has a number of joints exemplified by 118, 120, 122, 124. The joints provide sufficient articulation to position and rotate quadrupole magnet 12' around an operating region of a patient placed on patient support 11B. An articulated arm 116 suitable for this purpose will be found in commonly assigned application Ser. No. 09/189,633, filed Nov. 10, 1998, entitled "Articulated Magnetic Guidance Systems and Devices and Methods for Using Same for Magnetically-Assisted Surgery," which is hereby incorporated by reference in its entirety. Movement of articulated arm 116 may be manually controlled, or more preferably, robotically controlled, such as by computer-controlled servo systems, which may preferably be coordinated with a medical imaging system as well as one or more visual display systems and input systems to assist a surgeon guiding a magnetic implant influenced by quadrupole magnet 12'. Many of these systems are not shown in FIG. 7, but it will be understood that at least a medical imaging system such as one similar to that shown in FIG. 1 and described in conjunction therewith would normally be present and would be used during surgery.

Figure 8A:
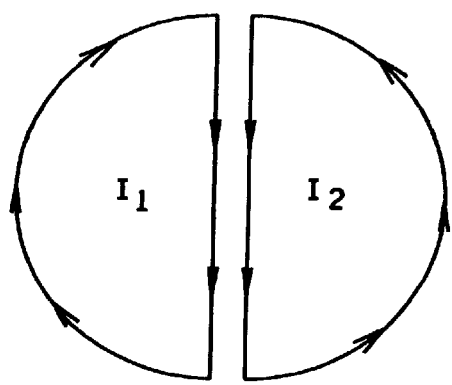
FIG. 8A is an illustration of a pair of oppositely-wound coils of a type suitable for use as the magnet of the system shown in FIG. 7.
Figure 8B:
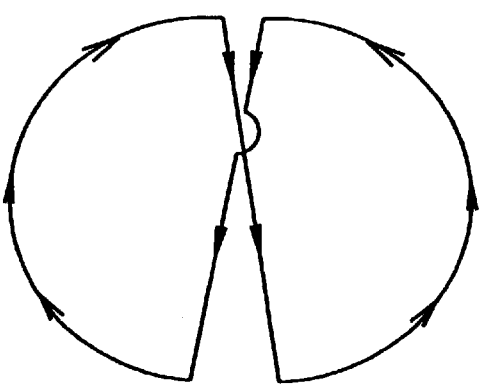
FIG. 8B is an illustration of a single, continuously-wound coil having a cross-over, the coil being of a type suitable for use as the magnet of the system shown in FIG. 7.
Figure 9:
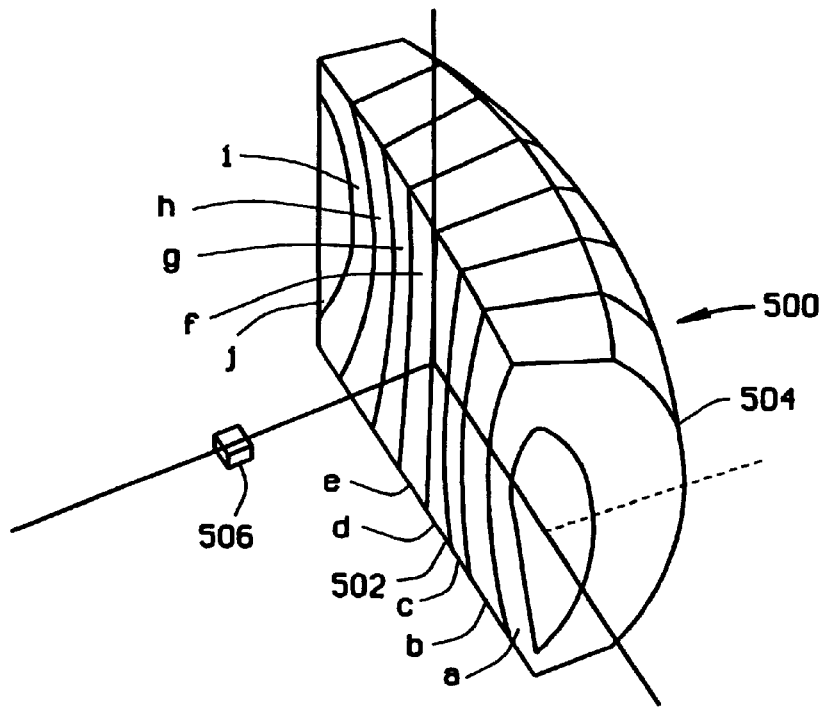
FIG. 9 is a perspective view of a compound magnet constructed according to the principles of this invention, and adapted for magnetic navigation in accordance with the principles of this invention.
Figure 10:
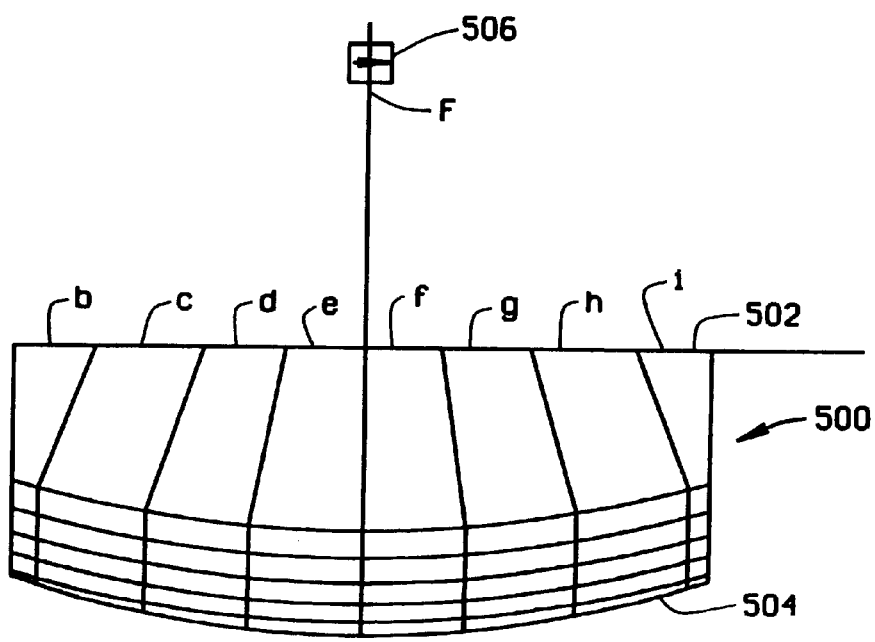
FIG. 10 is a top plan view of the compound magnet.
Figure 11:
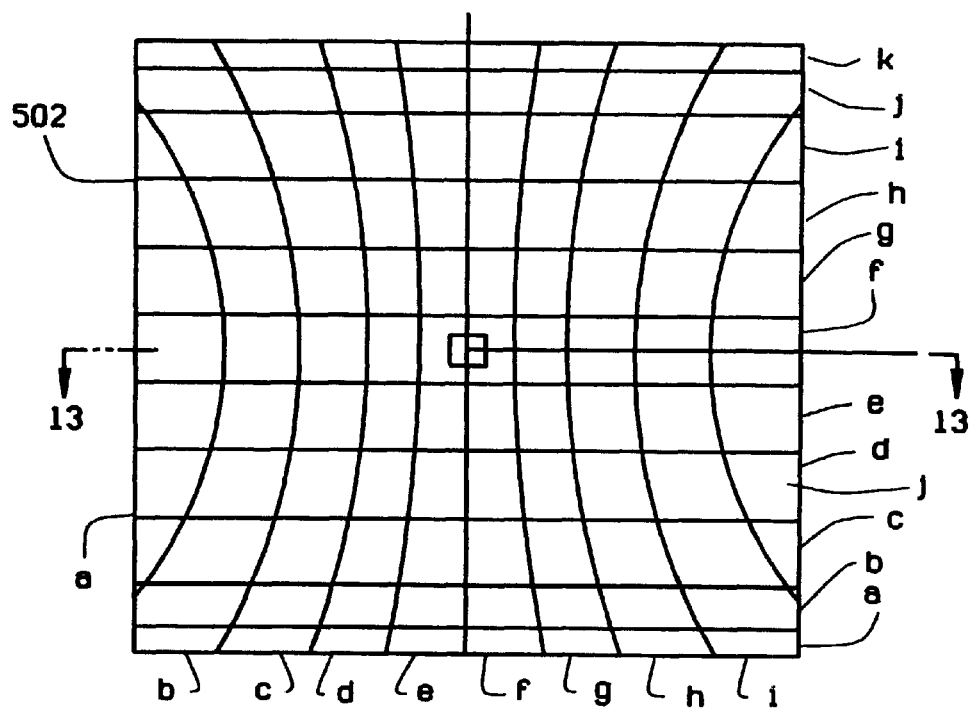
FIG. 11 is a front elevation view of the compound magnet.
Figure 12:
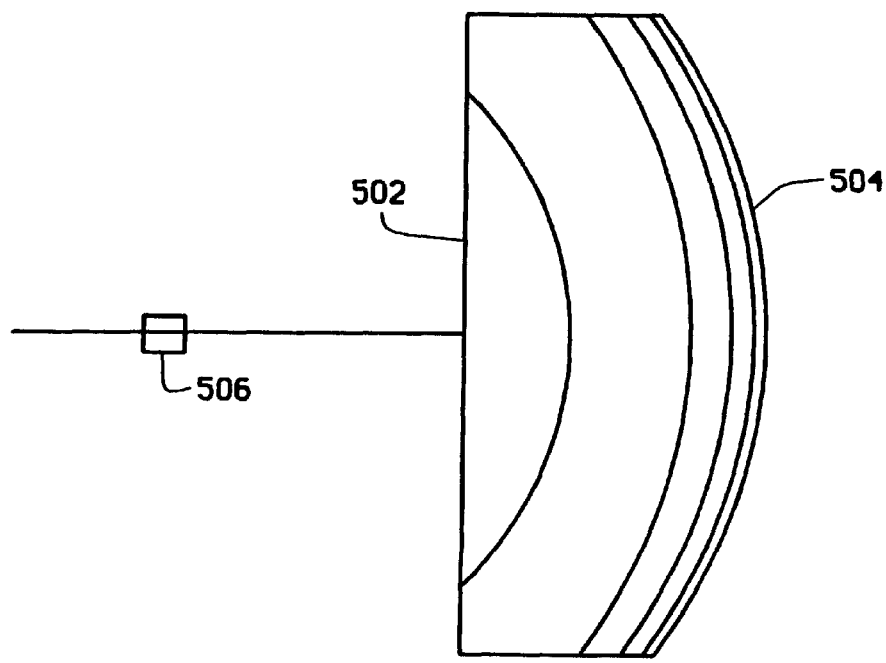
FIG. 12 is a side elevation view of the compound magnet.
Figure 13:
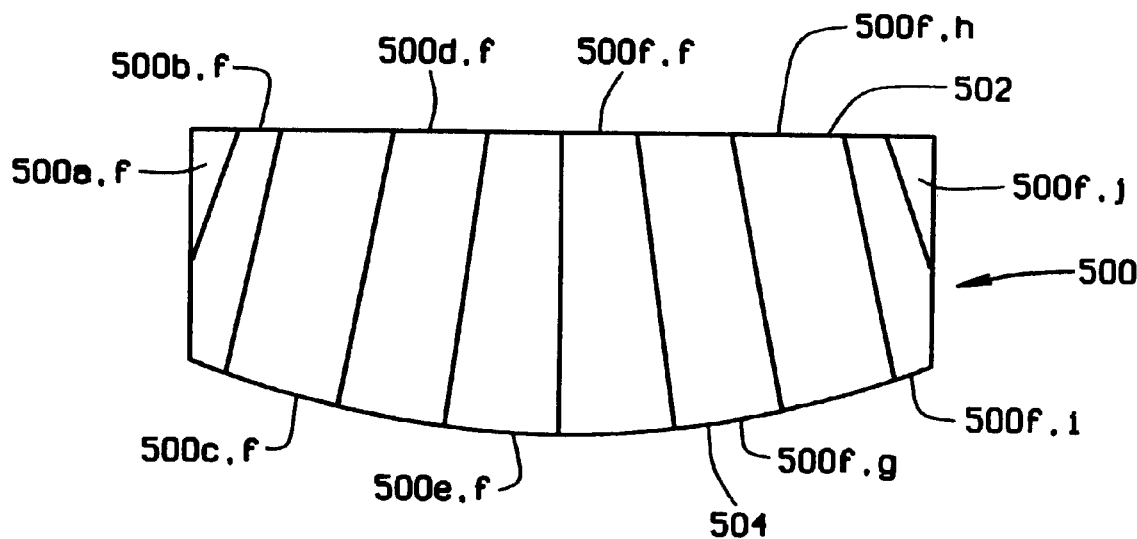
FIG. 13 is a horizontal cross sectional view of the compound magnet taken along the plane of line 13—13 in FIG. 11.

Coils 112 and 114 are oppositely wound, as shown in FIG. 8A, or a single, continuously-wound coil 112' with a cross-over, as shown in FIG. 8B, may be provided instead. Either of these coil arrangements will operate as a quadrupole magnet to generate transverse gradients, i.e., gradients having a pulling direction perpendicular to the direction of the magnetic field. The field and gradient of the electromagnetic quadrupole magnet 12' are similar in form to those of permanent magnet 12 shown in FIG. 1. An advantage of the permanent magnet quadrupole over a superconducting quadrupole electromagnet is that it is not necessary to provide cryogens for a permanent magnet. However, superconducting coils can have considerably greater strength for a given size and weight. If magnet 12' in FIG. 7 were superconducting, a cryogenic system (not shown) would have to be supplied. The design of a suitable cryogenic system could be accomplished by one skilled in the art, however, and is not considered part of the present invention.

Aside from the stronger magnetic fields obtainable from a superconducting quadrupole electromagnet, another advantage of an electromagnetic quadrupole magnet 12' is that the field strengths produced in the operating region of a patient may be controlled not only by repositioning magnet 12', but by controlling the currents in its coil 112' or coils 112 and 114. This reduces somewhat the need for movement of magnet 12' and possibly the need for certain types of articulation of articulated arm 116.

Although articulated arm 116 is shown in FIG. 7 as being suspended from a ceiling, it will be recognized that other mounting configurations that provide for stable movement and positioning of magnet 12' are also suitable. Also, it should be noted that other configurations of electromagnets that are effective in producing or emulating a multipolar magnetic field (i.e., one of more than 2 poles) may be used instead of the quadrupole example shown and described here. For example, an eight-pole electromagnet could be compactly formed from four coils wound in 90° pie-shaped sections assembled in a circular arrangement. However, absent special circumstances, a quadrupolar field should suffice for surgical applications. (It should be mentioned that a D-shaped section may be considered as a 180° pie-shaped section.)

An alternate construction of a permanent magnet useful in magnetic navigation is indicated generally as 500 in FIGS. 9–13. The magnet 500 has a front face 502 and a back face 504. The magnet 500 is specially constructed to provide a magnetic field F in a selected direction at a selected operating point 506 spaced from the front face 502 of the magnet. The operating point is at least about six inches (15.2 cm), and is preferably about eight inches (20.3 cm) from the front face. These distance appears to provide an appropriate balance between maximizing the strength of the magnetic field F at the operating point 506, and providing adequate room to translate and rotate the magnet 500 to magnetically navigate a medical device inside the patient's body, without impinging on the patient's body.

The front face 502 is preferably substantially flat to allow the magnet 500 to be positioned close to the patient, and to be translated and rotated without impinging on the patient. The back face 504 is generally curved, and preferably conforms substantially to a surface of constant contribution. A surface of constant contribution is the surface along which optimally aligned magnetic moments contribute equally to the magnetic field F. The actual shape of the back face 504 may vary insubstantially from the precise shape of the constant contribution surface, to make the manufacture of the surface easier, particularly in making and assembling the segmented construction of the magnet described more fully below. More specifically, the magnet may be comprised of a plurality of segments, and the segments at the back face may have flat faces (for manufacturing simplicity) that approximate the curved constant contribution contour or surface. A reason for shaping the back face 504 in accordance with the constant contribution surface is that this is the most weight and volume efficient way to maximize the magnetic field F at the operating point. It will always be more efficient from a weight and volume standpoint to add material inside a constant contribution surface, than to add material outside the constant contribution surface.

The magnet 500 is preferably divided into a plurality of segments of constant magnetization direction. Ideally, the magnet 500 would have a local magnetization direction at each point that maximizes this magnetic field F at the operating point 506. However such an ideal configuration would be difficult to practically obtain. Instead, the magnet is preferably divided into a number of segments of uniform magnetization. In accordance with one embodiment of the compound magnet of this invention, the magnet 500 is divided into segments, and the proper magnetization direction is determined for each segment. In accordance with an alternate embodiment of the magnet 500, the magnet is divided into segments of identical or similar magnetization direction.

In the former case, the magnetization direction can be determined, for example, by determining the location of the center of mass of a segment, and determining the magnetization at the location of the center of mass that maximizes the magnetic field F at the operating point 506. Alternately, an average direction can be determined form the direction of maximum contribution at each point within the segment, and preferably this average can be weighted by the relative contribution of the magnetization direction at each point to the field F.

In the later case, various algorithms can be used to divide the magnet into segments of constant or near constant (i.e. that do not vary by more than a pre-determined threshold) direction of magnetization.

Figure 18:
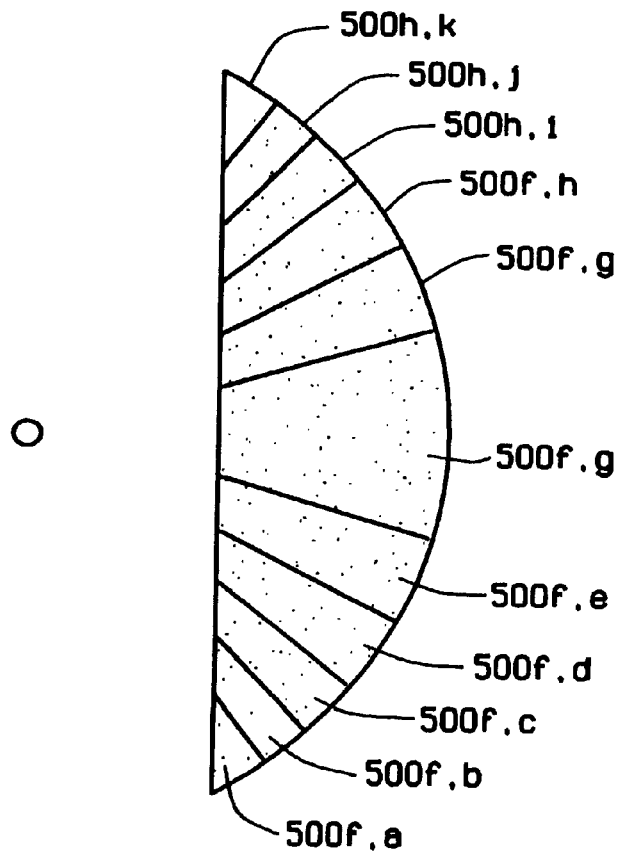
FIG. 18 is a diagram showing the magnet in vertical cross-section of the magnet taken along the plane of line 18—18 in FIG. 17.
Figure 14:
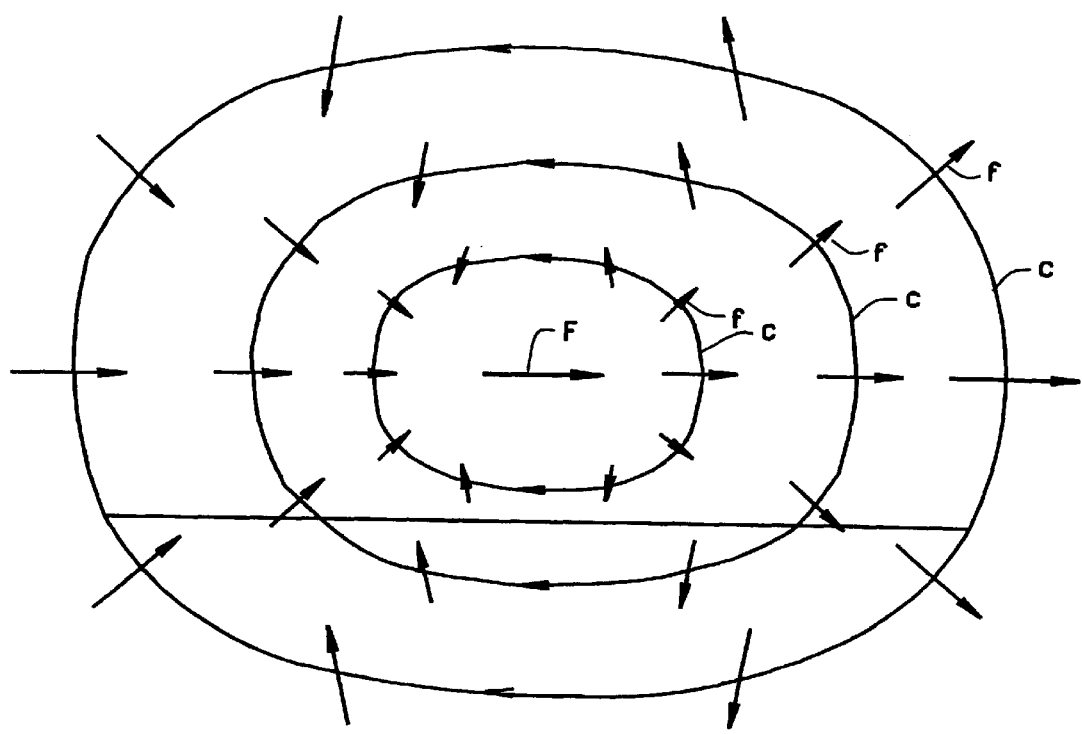
FIG. 14 is a diagram showing the desired magnetic field F at the operating point, and the surrounding contours of constant field contribution, and arrows indicating optimal moment direction.
Figure 15:
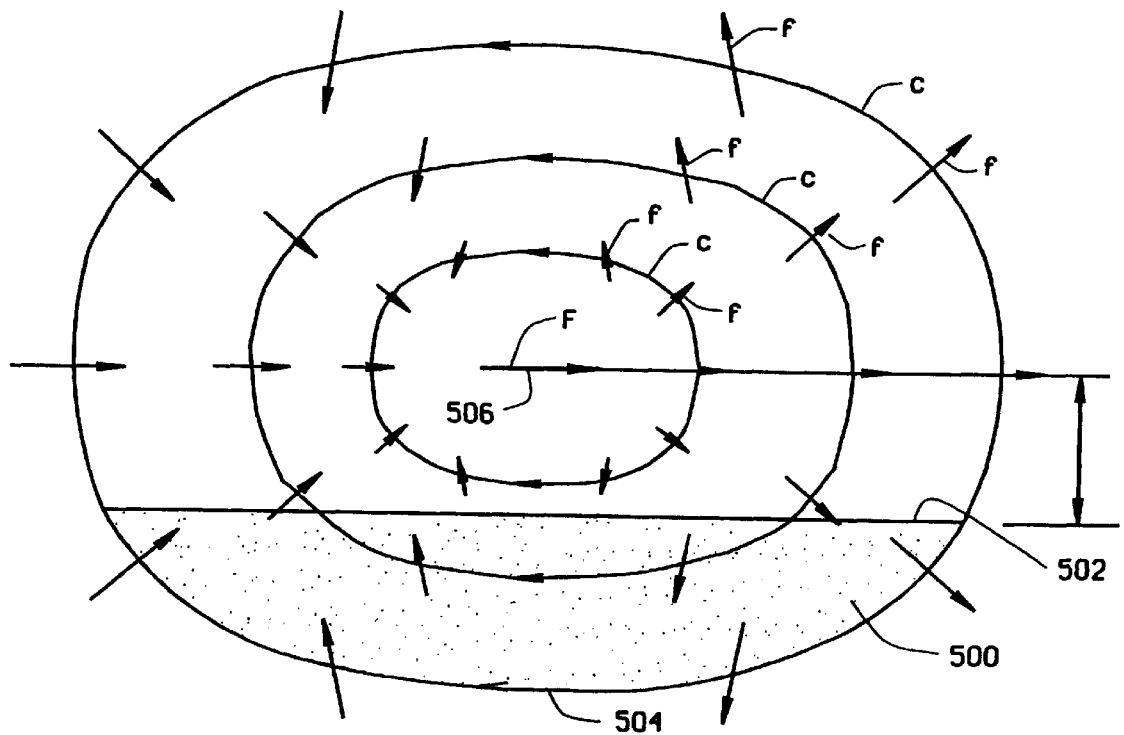
FIG. 15 is a diagram showing the ideal shape and local magnetization directions at the horizontal cross-section of a magnet to achieve the desired magnetic field F.
Figure 16:
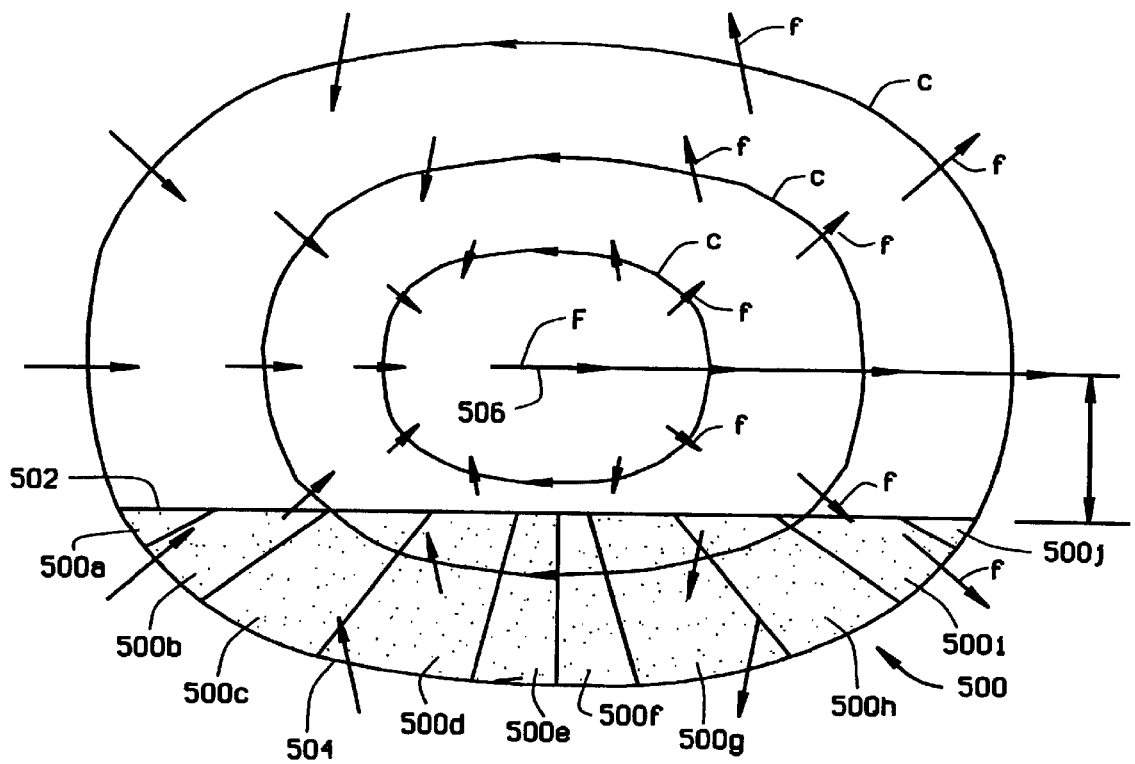
FIG. 16 is a diagram showing the ideal shape and local magnetization directions of a magnet at the horizontal cross-section to achieve the desired magnetic field F, after division into a plurality of segments.
Figure 17:
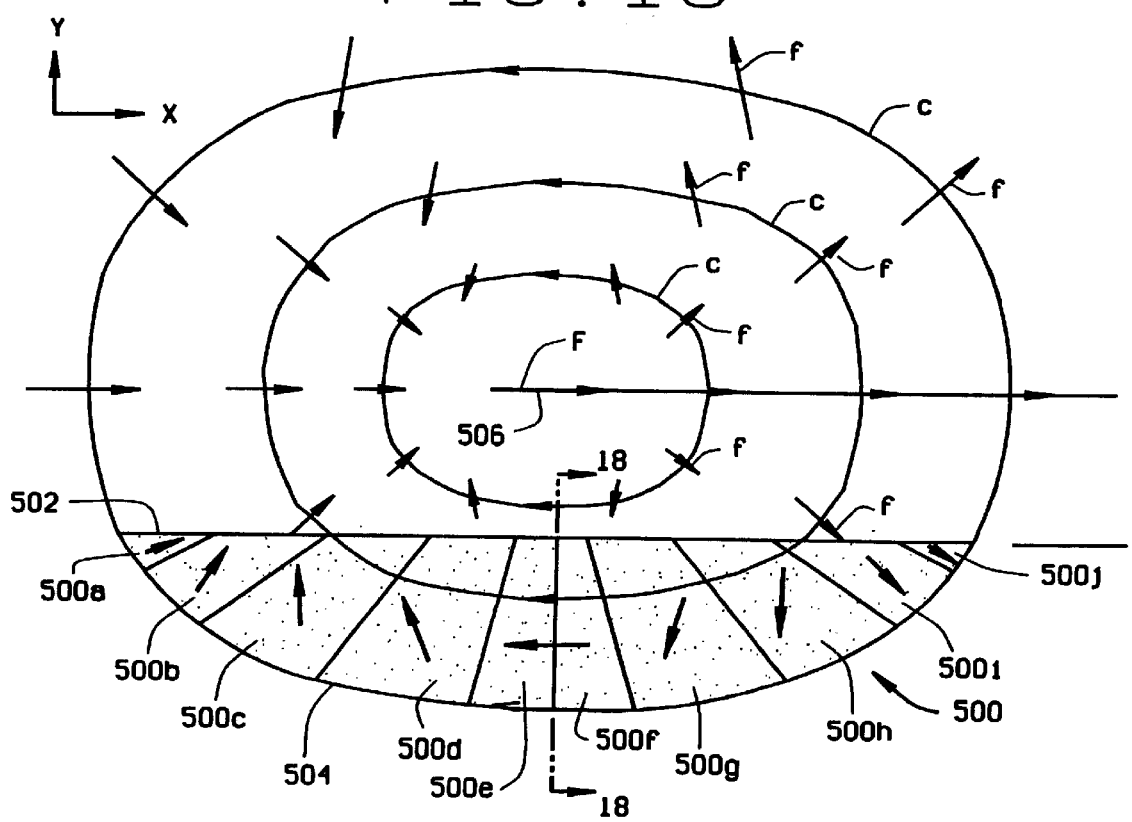
FIG. 17 is a diagram showing the magnet after division into a plurality of segments at the horizontal cross-section, with a selected uniform magnetization to approximate the ideal local magnetization direction.

The ideal orientations of the directions of magnetization within the magnet is illustrated in FIG. 14, where the desired field F at the operating point is shown surrounded by a series of constant field strength curves C, with the local field directions indicated by arrows f. As shown in FIG. 15, the magnet 500 is constructed by selecting the desired distance between the operating point 506 and the front face 502 of the magnet. As shown in FIG. 15 the desired shape of the magnet 500 has the flat front face 502 (for accommodating translations and rotations while minimizing impacts with the patient), and a curved back face 504, which generally conforms to the curve of constant field strength, and which also represents lines of constant contribution to the desired magnetic field F. As shown in FIG. 16 the desired magnet shape is divided up into segments For manufacturing convenience the segments preferably have flat sides, and the flat sides forming the back face of the magnet approximate the constant contribution contour, although there will be some variance that increases as the size of the segments increases. As shown in FIG. 17, an appropriate uniform magnetization direction for the magnet segment is determined. As shown in FIG. 18 vertical cross-section of the magnet, the magnets are divided vertically and horizontally into segments.

In the preferred embodiment shown in the Figures, magnet 500 is divided into ten vertical columns a through j, and is divided into eleven horizontal rows a through k, for a total of 110 segments. Each segment can be identified by its column and row, thus the segments of the preferred embodiment can be defined as 500 a,a through 500 j,k. Of course, the magnet can be divided into a smaller number of segments or a greater number of segments. There is a cost balance between the improved properties using smaller, and thus more, segments, and the cost of manufacturing and assembling the segments.

The direction of magnetization in each of these segments 500 a,a though 500 j,k is the direction of magnetization at the location of the center of mass of the segment. Thus, for example, the center of mass of segment 500 a,a is determined, and the magnetization direction is determined for the location of the center of mass that will provide the maximum contribution to the desired field F. This direction is then applied to the entire segment. Of course, some other method of determining the magnetization direction for each segment to substantially approximate the maximum contribution of the segment to the desired magnetic field F.

Generally each segment will have a front face, a back face, and a sidewall comprising one or more sides. The sides of the segment generally planer (to facilitate manufacture of the segments and their assembly into a compound magnet), and these sides generally coverge toward the operating point 506. The magnet can be divided into fewer or more segments, the segments can also be layered, with the shape of the front and back of each layer corresponding to a contant contribution surface, so that the thickness of each layer of segments corresponds to a range to contribution to the desired magnetic field F.

The magnet 500, made from a ten by eleven array of segments 500 a,a 500 j,k made NdBFe 5062, with a front face 502 of 18 inches (45.7 cm) by 18 inches (45.7 cm), and an operating point 9 inches (22.9 cm) from the front face would have a total weight of 511 pounds. The magnet 500 would be capable of generating a magnetic field F of 0.1 T, at the operating point 506, 9 inches from the face 502. In contrast, a conventional cylindrical bi-polar magnet of the same material would have to have dimensions of 24 inches in diameter, and 16 inches high, and have a weight of 2100 pounds in order to generate a comparable magnetic field at a comparable distance. Thus the magnet 500 can generate a magnetic field that is usable for magnetic navigation inside the body with a much small volume and weight than conventional magnets, and this smaller, lighter magnet is easier to manipulate (translate and rotate) as needed during the magnetic navigation procedure.

Figure 19A:
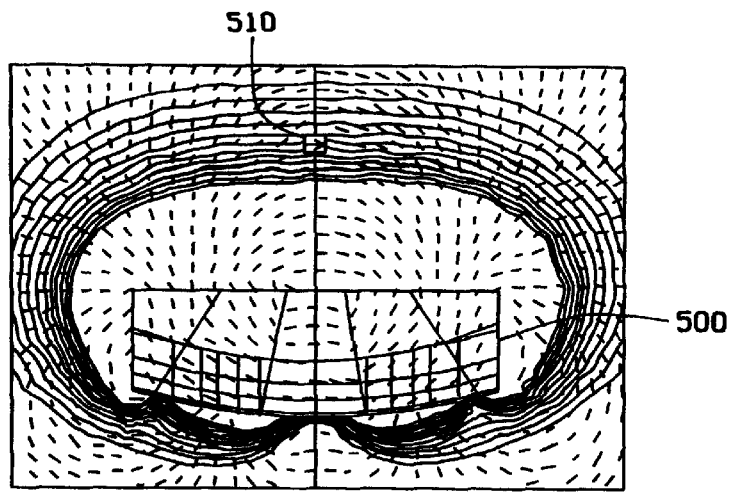
FIG. 19A is a top plan view of the magnet showing the field created by the magnet in an operation region in a patient.
Figure 19B:
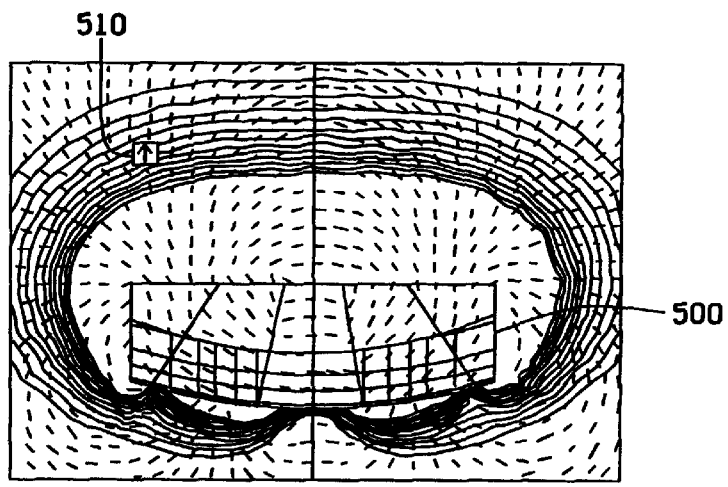
FIG. 19B is a top plan view of the magnet showing the field created by the magnet in an operating region in a patient after a translation in a first direction.
Figure 19C:
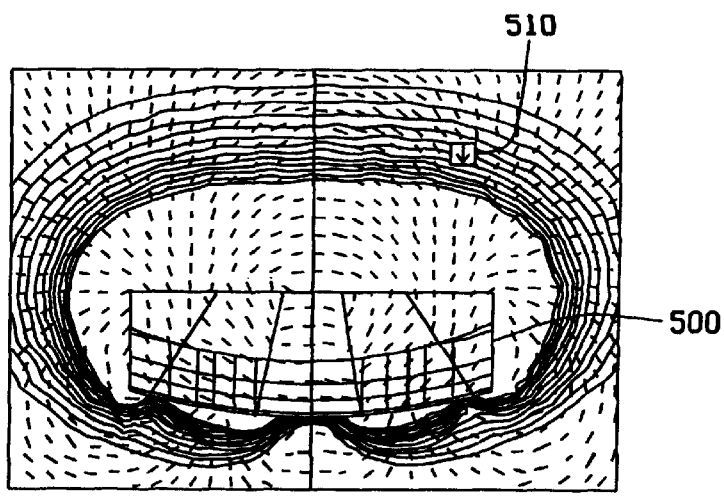
FIG. 19C is a top plan view of the magnet showing the field created by the magnet in an operating region in a patient after translation in a second direction.
Figure 19D:
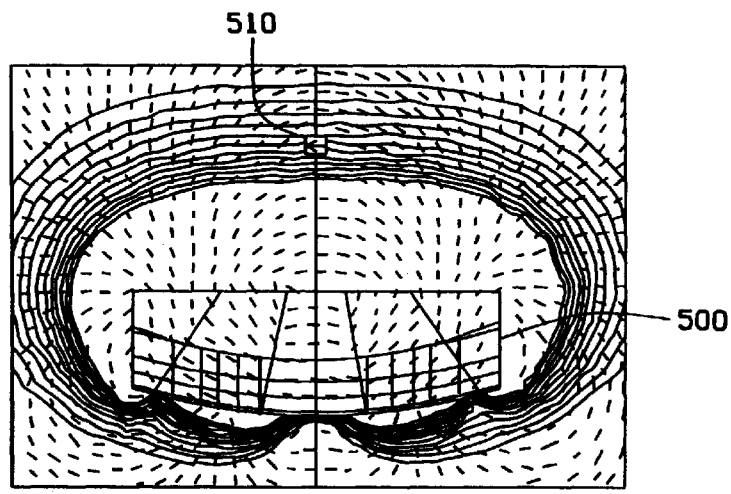
FIG. 19D is a top plan view of the magnet showing the field created by the magnet in an operation region in a patient after a rotation.

Moreover the magnet 500 provides a more desirable field directions for magnetic navigation. A simple transverse translation causes the direction of the magnetic field at the operating point to change. For example, as shown in FIG. 19A, the magnet 500 creates a magnetic field F in an operating region 510 inside the patient, generally parallel to the front face 502 of the magnet. In FIGS. 19A and 19D, the operating point 506 of the magnet and the operating region 510 inside the patient coincide. However, by translating the magnet 500 to the right, the magnetic field direction in the operating region in the patient changes, as shown in FIG. 19B. Similarly, by translating the magnet 500 to the left the magnetic field direction in the operating region in the patient changes, as shown in FIG. 19C. Finally, by simply rotating the magnet 500 (about the line between the front face 502 and the operating point 506), the direction of the field can be reversed, as shown in FIG. 19D.

Thus by a combination of translations and rotations of the magnet 500, a navigating magnetic field of any orientation can be created in an operating region in a patient for orienting a magnetic medical device inside the patient. A system for translating and rotating the magnet 500 might include a robotic support manipulator. Because of the weight of the magnet 500 and for other reasons, as well, robotic control is preferable to full manual movement of magnet 500, although manual control is both possible and contemplated within the scope of the invention. The movements required of the robotic manipulator are those that are required to make possible the rotations and translations needed to achieve orient the magnetic field in the operating region in the patient in any direction that the physician may want to orient a magnetic medical device inside the operating region inside a patient.

Robotic manipulators are well-known in the art, and the design of servo mechanisms to provide the needed movements of magnet 500 would present no special difficulties to one skilled in that art. Such servo mechanisms could be manually controlled by a surgeon viewing real-time medical images of the operating region of a patient, or could be automatically controlled by a computer interpreting such images. If manually controlled, a computer could provide assistance by displaying medical images of the operating region of the patient, showing the magnetic delivery vehicle (MDV) or magnetic seed in the patient with other useful information superimposed or adjacent to this image. This other information could include a desired path of the MDV or magnetic seed and the magnetic field lines or gradient of magnet 500.

Figure 24:
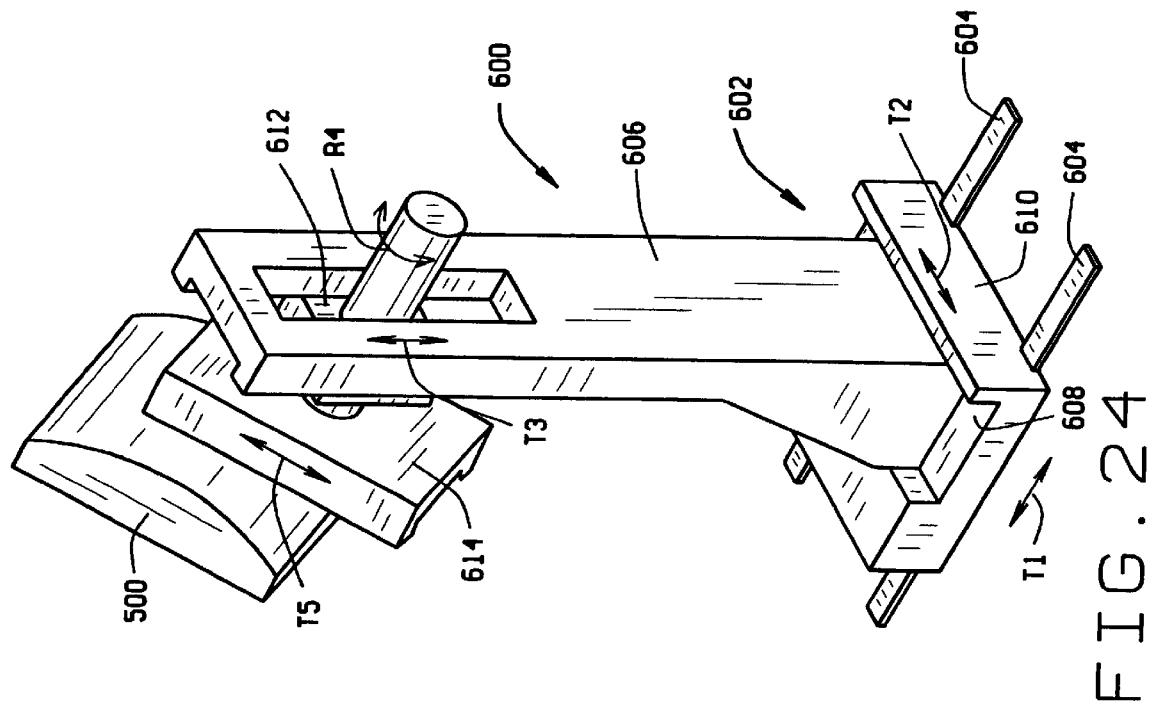
FIG. 24 is a rear perspective view of the support.
Figure 23:
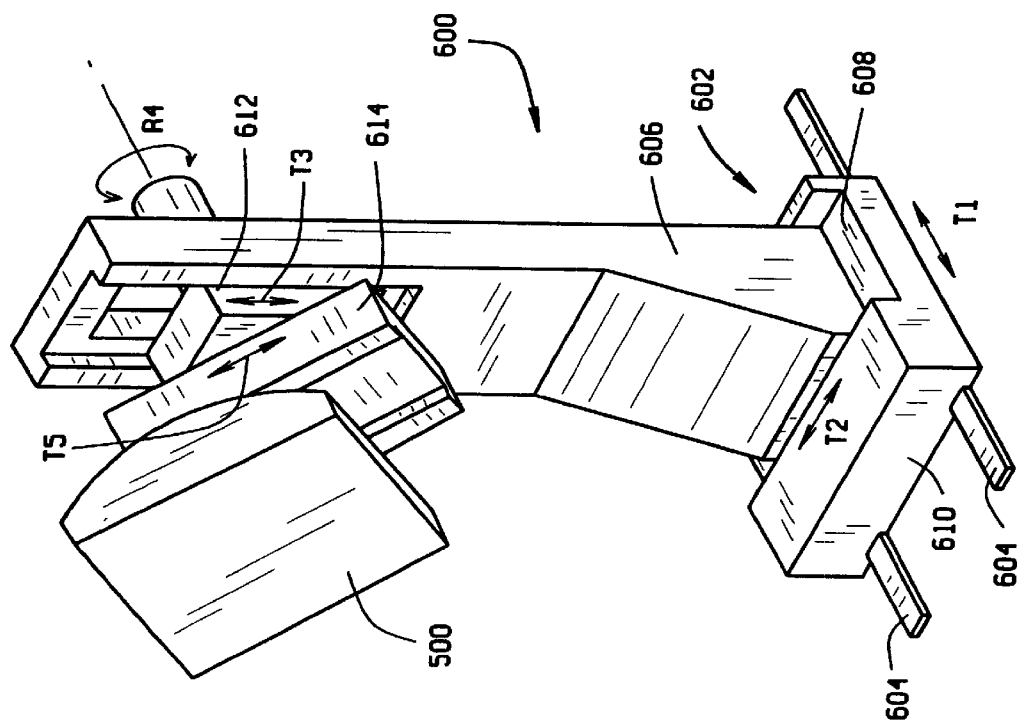
FIG. 23 is a front perspective view of a support for the permanent magnet.

A device for manipulating the magnet is indicated generally as 600 in FIGS. 23 and 24. As shown in FIGS. 23 and 24, the device 600 comprises a support 602 that is mounted on tracks 604 for movement toward and away from the patient, providing the first translation indicated by the double headed arrow T1. The support 602 comprises a vertical stanchion 606 slidably mounted in a track 608 in a base 610. The movement of the vertical stanchion in the track 608 provides a second translation, indicated by the double headed arrow T2, generally perpendicular to the first translation T1. A bracket member 612 is slidably mounted on the vertical stanchion 606, for vertical movement, proiding a third translation indicated by the double headed arrow T3. The magnet 500 is slidably mounted to a magnet arm 614, and the magnet arm is rotatably mounted to the bracket member 612, for rotation about a generally horizontal axis. This provides a rotation indicated by the doubled headed arrow R4. The magnet 500 can slide relative to the magnet arm 614, providing a fourth translation, indicate generally by the double headed arrow T5. Thus the support 600 provides five degrees of freedom translations T1, T2, T3, and T5, and rotation R4, to position the magnet 500 relative to the patient, to control the direction and magnitude of the magnetic field in the operating region in the patient.

Figure 25:
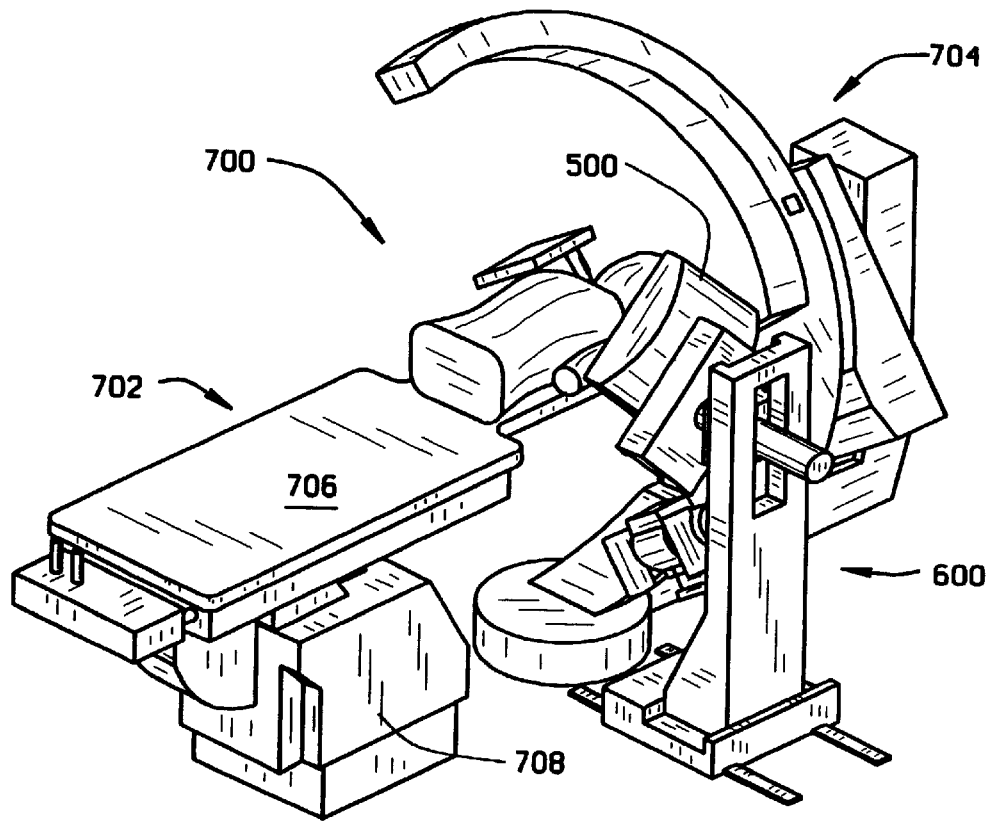
FIG. 25 is a perspective view from the right side of a magnetic surgery system incorporating the magnet and support.
Figure 26:
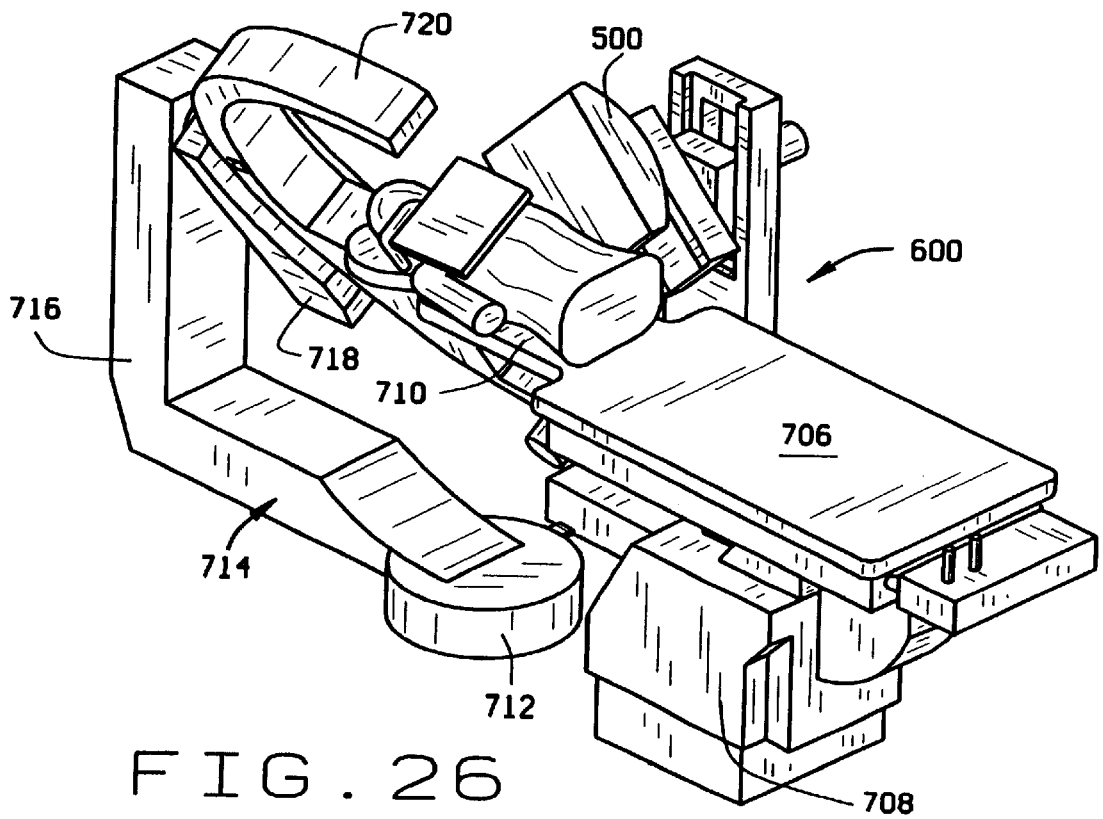
FIG. 26 is a perspective view from the left side of a magnetic surgery system incorporating the magnet and support.

The device 600 is preferably part of a larger magnetic surgical system indicated generally as 700 in FIGS. 25 and 26. The system 700 includes a patient support 702, and imaging system 704, and the device 600 for manipulating the magnet 500. The patient support 702 comprises a bed 706 that is supported at a convenient operating level by a base support 708. Bed 706 includes a region 710 that is or can be brought into proximity with magnet 500. (Although it is contemplated that the magnet 500 will be moveable, movement of the operating region of a patient relative to magnet 500 may alternately, in some circumstances, be accomplished by moving the bed 706 supporting the patient.) The imaging system 704 comprises a rotating pivot or swiveling support 712 on which is attached an imaging assembly 714 comprising a base frame 716, arcuate support 718, and arcuate section 720. Part of imaging assembly 714 may comprise any suitable, commercially available C-arm assemblies, such as those made by General Electric Co. of Syracuse, N.Y., however, it is not required that the "arcuate" section be in the shape of an arc. Because commercially available C-arm assemblies usually are this shape, however, it is convenient to use this terminology. Support 712 need not be mounted or free-standing on a floor, as shown here. Some other mounting possibilities include attachment of support 712 to an extension of base support 708 of patient support 702, or to an extension of base 610 of device 600. Mountings that do not require movements of imaging assembly 704 that interfere with the attached imaging apparatus described below when magnet 500 is repositioned are preferable.

Arcuate section 720 supports one or more X-ray or fluoroscopic tubes for use in providing a medical image of the operating region of the patient supported at region 710 of bed 706. Thus, each of the tubes have their beams aimed at corresponding imaging plates through this region. Preferably, imaging plates are held in place by imaging plate supports, which are separate supporting arms. The position of these plates may be adjusted somewhat by moving blocks which are configured to slide (such as on tracks), over surfaces of a pie-shaped portion of arcuate support 720.

Some of the pivoting and movement mechanisms of the C-arm and imaging assembly 704 are not shown in FIG. 1, but are shown and described in U.S. patent application Ser. No. 09/211,723, incorporated herein by reference. Briefly, arcuate section 720 is configured to provide various views of an operating region of a patient by pivoting at swivel support 712, partial rotation around another pivot (i.e. of arcuate support 718 relative to arm 716), and by partial rotation of the entire arcuate section 720 around a central point, (relative to arcuate support 718). Each movement of arcuate section 720 also causes the imaging tubes and their respective imaging plates to move correspondingly relative to the operating region of the patient, which is not operatively coupled to these C-arm movements. Thus, various views of the operating region are available.

It will be observed that movement of the arcuate section 720 and the objects attached to it result in physical exclusion volumes being created. These are regions of space that are or may be occupied by the moving components, and that must therefore be avoided by, movements of the magnet 500 or device 600. If the physical exclusion volumes are not respected, physical interference between the components of the system occur. It may also be useful to consider magnetic as well as physical exclusion regions. Magnetic exclusion regions are regions from which, taking into account the movement of magnet 500, magnetic objects or objects that may be adversely affected by magnetic fields should be excluded. Thus, it may be desirable to avoid placing some types of imaging plates within a region of high field strength of magnet 500. However, because of the compact size and focused field of the magnet 500, and the requirement of only limited rotational and translational movement, both its physical and magnetic exclusion zones are advantageously quite small. Additionally, because of the configuration of magnet 500, the magnetic exclusion zone is smaller than might otherwise be the case, because the magnetic field generally drops off more quickly with distance for such magnets than with simple dipole magnets and solenoids previously used.

The inventive system described herein is intended 20 for use in magnetically assisted surgery. For example, it may be used to guide a tiny magnet on the end of a catheter or guide wire that is magnetically navigated into an aneurysm in the brain. A magnetic medical device, as may be introduced into an operating region of a patient in accordance with this invention. The magnet 500 can be manipulated using device 600 to selectively orient the magnets on the magnetic medical device, and thus orient the magnetic medical device itself. The medical device can then be mechanically moved in the desired direction (either by manually or robotically pushing or pulling).

The device 600 and the patient support 702 as shown and described herein are physically separate assemblies, but it should be clear that this is not a requirement of the invention. It is also not necessary that patient support 702 be in the form shown here. Any form of supporting structure suitable for holding or supporting an operating region of a patient may be used, possibly including a floor in an emergency, with suitable modification of either or both 600 and imaging assembly 704 so that the magnet 500 may be appropriately positioned and the operating region properly imaged. In the claims appended below, it should be understood that a magnet support structure and a patient support structure need not be physically separate assemblies, and that, unless explicitly stated otherwise, the magnet support structure and patient support structure may comprise different portions of a single structure.

In alternate embodiments, a magnet may be attached to a flexible or articulated arm that is attached to the ceiling, rather than to a support structure that is attached to or supported by the floor. A ceiling mounted assembly would avoid congestion at the floor area of the patient. Moreover, the flexible or articulated arm may be designed to allow easy manual or adjustment of the position and angle of the magnet assembly. Alternately, the ceiling supported assembly could be robotically controlled.

Operation

In addition to providing stronger fields that other magnets of comparable size, magnet 500 is capable of being used for magnetic navigation by relatively simpler methods. Any type of turn of a magnetic medical device inside a patient's body smoothly and continuously, without coning, with one rotation and two translations. That is the magnet 500 can effect a safe and efficient turn, i.e., one in which the vector representing the direction of the magnetic medical device turns in a plane represented by the initial and final vectors. Without sufficient attention, turns can be made with some magnetic navigation systems in which the direction deviates from the plane significant, generally describing some section of a cone, which can be injurious to surrounding tissues.

Any pair of vectors depicting the position of the desired field directions before and after a turn in the operating region of a patient will lie in a plane. The magnet 500 will need to be rotated so that its midplane (the horizontal plane through the center of the magnet) coincides with the plane of the turn. If the operating (turning) point is not on the central axis of the magnet, the magnet 500 will also have to be translated so the unique plane can be both parallel to the turn plane and contain the operating point, without tilting the magnet central axis.

Figure 20:
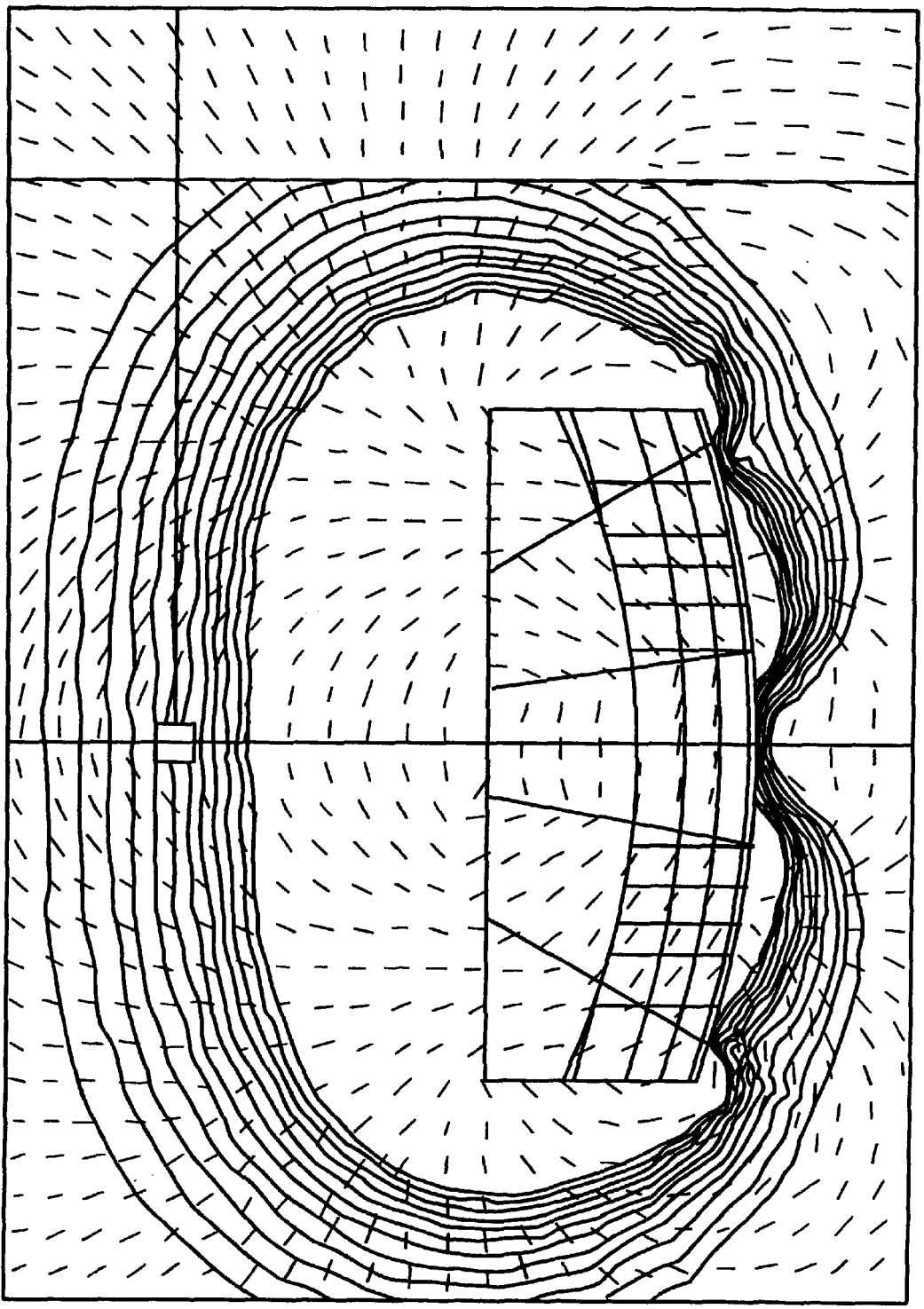
FIG. 20 is a horizontal cross-sectional view of the magnetic showing the magnetic field lines.
Figure 21:
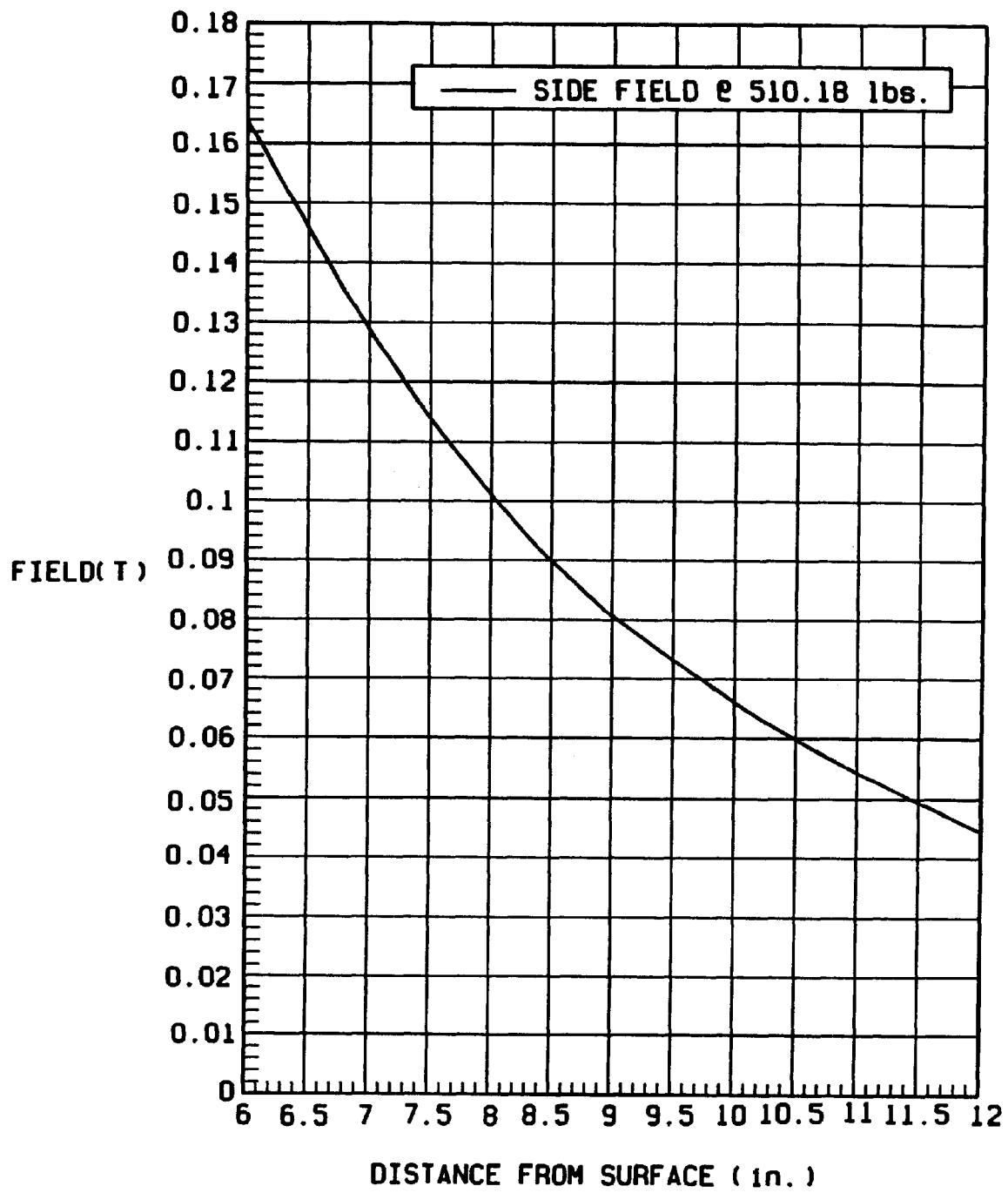
FIG. 21 is a plot of field strength versus distance from the magnet.

FIG. 20 shows a detailed and accurate plot of the magnetic field lines as a quiver diagram, and contours of constant field strength. Three representative types of turns will be described, referencing FIG. 22, which show a simplified diagram of the magnet. A magnetic medical device is located at point P1 in the magnetic field of magnet 500. To make a 90° clockwise turn in the horizontal plane, a movement of the magnet to the left, so that the position of the magnetic medical device in the field of the magnet moves from point P1 to point P2 will accomplish this. Thus a single translation of magnet 500 is sufficient to make this turn. A magnetic medical device is located at point R4 in the magnetic field of magnet 500. To make a 180° turn in the horizontal plane, a move of the magnet to the right, so that the position of the magnetic medical device in the field of the magnet moves from R4 to R3 along line A, will accomplish this. Thus, single translation of magnet 500 is sufficient to make this turn. A magnetic medical device is located at point S3 in the magnetic field of magnet 500. To make a 180° turn in the horizontal plane, a pure translation of the magnet to the left would bring the operating point to the right in the frame of the magnet, to point R4 where it will have turned 90° clockwise. Now the magnet 500 can be rotated about an axis through that point R4, and parallel to the main axis of the magnet, without tilting the magnet, or "coning" the magnetic medical device in the patient. The magnet will be rotated 180° about this axis. From an observer's view above the patient, all the magnetic field directions will appear to be reversed, then the previous translation is reversed, bringing the magnet from R4 to S3, but the direction will have been reversed.

Figure 22:
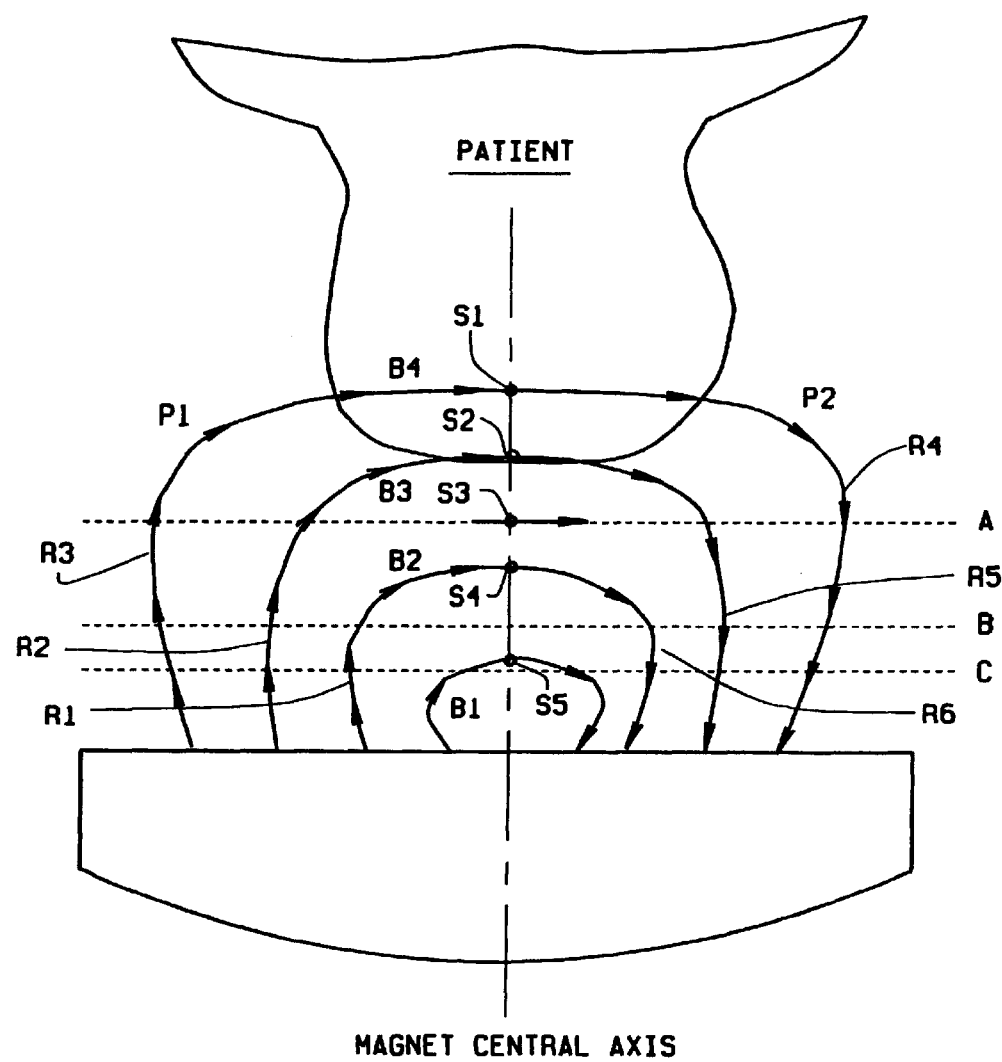
FIG. 22 is a diagram for the position of the magnet relative the patient, illustrating the use of the field to turn a magnetic medical device in a patient.

Any change in direction in the mid-plane of the magnet 500 can be accomplished by two translations and one rotation, as long as the minor field strength changes associated with the distance form the magnet central axis can be ignored. As shown in FIG. 20, the constant field contours are broad, and the changes of FIG. 22 are considerably exaggerated in order to illustrate navigation procedures. However, where it is necessary to account for field strength, this can be done. As shown in FIG. 22 only one magnetic field line, line B3, leaves and returns to the magnet face perpendicular to the face. But each plane, e.g. A, B, and C, will have two locations along their lengths at which the field line is perpendicular to the plane. FIG. 22 shows that points R4, R5, and R6 are such points where the field points toward the magnet 500, and that points R1, R2, and R3 are such points where the field points away from the magnet. These points form a locus line which bends outward, away from the central axis of the magnet as the operating position moves away from the magnet face. If the field strength, moving outward from the magnet central axis becomes too small, the magnet can be translated toward the patient, and an adjustment to the field vector turn can be made (which can be easily determined by computer). This is a complication, but it may not be necessary in most applications.

It will be understood that embodiments incorporating subsets of the inventive concepts herein disclosed are possible that provide some but not all of the advantages of the invention or that meet or satisfy one or more but not all of the objects of the invention. In addition, many modifications of the inventive embodiments disclosed herein will be apparent to those of ordinary skill in the art. Therefore, the scope of the invention should be determined as provided by the claims below, including the full range of equivalents provided under applicable laws.

What is claimed is:

1. A magnet having a front and a back face and comprising a plurality of segments, the segments each magnetized to provide substantially the maximum magnetic field in a selected direction at an operating point spaced from the front face the back face being substantially contoured to follow a surface of constant contribution to magnetic field in the selected direction at the operating point, wherein each segment has a front face oriented toward the front face of the magnet, a rear face oriented toward the rear face of the magnet, and a sidewall, comprising at least one side, therebetween, the sides configured to converge toward the operating point.

2. The magnet according to claim 1 wherein the magnet comprises a plurality of layers of segments between the front face and the back face.

3. The magnet according to claim 2 wherein each layer is substantially bounded by a surface of constant contribution to the magnetic field in the selected direction at the operating point.

4. A magnet for applying magnetic field in a selected direction at a selected operating point, the magnet comprising a front face generally facing the operating point, and a back face facing away from the operating point, the back face generally conforming to a constant contribution surface of the magnetic field in the selected direction, wherein the magnet is divided into a plurality of segments, with each segment further having a sidewall comprising at least one side extending between the front face and the back face, and wherein the sidewalls converge toward the operating point.

5. The magnet according to claim 4 wherein there are a plurality of layers of segments, each layer generally conforming to a range of constant contribution to the magnetic field in the selected direction.

6. The magnet according to claim 5 wherein each segment is magnetized in the direction of magnetization that, at the center of mass of the segment, provides the maximum contribution to the magnetic field in the selected direction at the selected operating point.

7. The magnet according to claim 5 wherein the selected operating point is at least six inches from the front face of the magnet.

8. The magnet according to claim 5 wherein the selected operating point is at least eight inches from the front face of the magnet.

9. The magnet according to claim 5 wherein the front fact is substantially flat.

10. The magnet according to claim 4 wherein each segment is magnetized in the direction of magnetization that, at the center of mass of the segment, provides the maximum contribution to the magnetic field in the selected direction at the selected operating point.

11. A magnet for applying a magnetic field in a selected direction at a selected operating point, the magnet having a generally flat front face facing the operating point, a curved back face facing away from the operating point, the magnet comprising a plurality of segments, each of which is magnetized in the direction that, at the center of mass of the segment, provides the maximum contribution to the magnetic field in the selected direction at the selected operating point.

12. The magnet according to claim 4, wherein each segment comprises a front face, generally facing the operating point, the back face generally facing away from the operating point, the back face generally conforming to a constant contribution surface of the magnetic field in the selected direction.

13. The magnet according to claim 12 wherein each segment is magnetized in the direction of magnetization that, at the center of mass of the segment, provides the maximum contribution to the magnetic field in the selected direction at the selected operating point.

* * * * *